US011931418B2

(12) United States Patent
Cleland et al.

(10) Patent No.: US 11,931,418 B2
(45) Date of Patent: Mar. 19, 2024

(54) METHODS OF TREATING SEVERE INFLAMMATION

(71) Applicant: Ashvattha Therapeutics, Inc., Redwood City, CA (US)

(72) Inventors: Jeffrey L. Cleland, Redwood City, CA (US); Kannan Rangaramanujam, Novi, MI (US); Sujatha Kannan, Redwood City, CA (US); Jay Zaveri, Redwood City, CA (US)

(73) Assignee: Ashvattha Therapeutics, Inc., Redwood City, CA (US)

( * ) Notice: Subject to any disclaimer, the term of this patent is extended or adjusted under 35 U.S.C. 154(b) by 175 days.

(21) Appl. No.: 17/240,558

(22) Filed: Apr. 26, 2021

(65) Prior Publication Data

US 2021/0353762 A1  Nov. 18, 2021

Related U.S. Application Data

(60) Provisional application No. 63/015,131, filed on Apr. 24, 2020.

(51) Int. Cl.
| | | |
|---|---|---|
| *A61K 47/60* | (2017.01) | |
| *A61K 9/00* | (2006.01) | |
| *A61K 9/19* | (2006.01) | |
| *A61K 31/198* | (2006.01) | |
| *A61K 45/06* | (2006.01) | |
| *A61P 29/00* | (2006.01) | |

(52) U.S. Cl.
CPC ............ *A61K 47/60* (2017.08); *A61K 9/0019* (2013.01); *A61K 9/19* (2013.01); *A61K 31/198* (2013.01); *A61K 45/06* (2013.01); *A61P 29/00* (2018.01)

(58) Field of Classification Search
CPC ........ A61K 47/60; A61K 9/0019; A61K 9/19; A61P 29/00
See application file for complete search history.

(56) References Cited

U.S. PATENT DOCUMENTS

| | | | |
|---|---|---|---|
| 8,889,101 | B2 | 11/2014 | Kannan et al. |
| 2006/0275838 | A1 | 12/2006 | Ray et al. |
| 2011/0034422 | A1 | 2/2011 | Kannan et al. |
| 2012/0003155 | A1 | 1/2012 | Dai et al. |
| 2012/0070432 | A1 | 3/2012 | Wiezorek et al. |
| 2013/0004427 | A1 | 1/2013 | El-Sayed et al. |
| 2013/0136697 | A1 | 5/2013 | Kannan et al. |
| 2017/0119897 | A1 | 5/2017 | Hackam et al. |
| 2017/0119899 | A1* | 5/2017 | Kannan .............. A61K 49/0054 |
| 2017/0173172 | A1 | 6/2017 | Mangraviti et al. |
| 2018/0264127 | A1 | 9/2018 | Ashford et al. |
| 2023/0226199 | A1 | 7/2023 | Cleland et al. |
| 2023/0233696 | A1 | 7/2023 | Cleland et al. |

FOREIGN PATENT DOCUMENTS

| | | |
|---|---|---|
| CN | 105879055 A | 8/2016 |
| KR | 101918346 B1 | 11/2018 |
| WO | WO 2009/046446 A2 | 4/2009 |
| WO | WO 2010/147831 A1 | 12/2010 |
| WO | WO 2011/044230 A2 | 4/2011 |
| WO | WO 2011/053618 A2 | 5/2011 |
| WO | WO 2015/168347 A1 | 11/2015 |
| WO | WO 2015/177279 A1 | 11/2015 |
| WO | WO 2016/025741 A1 | 2/2016 |
| WO | WO 2016/025745 A1 | 2/2016 |
| WO | WO 2019/071153 A1 | 4/2019 |
| WO | WO 2019/094952 A1 | 5/2019 |
| WO | WO 2020/110126 A1 | 6/2020 |
| WO | WO 2020/132196 A1 | 6/2020 |
| WO | WO 2021/113651 A2 | 6/2021 |
| WO | WO 2021/113657 A1 | 6/2021 |
| WO | WO 2021/217131 A1 | 10/2021 |
| WO | WO 2022/016120 A1 | 1/2022 |

OTHER PUBLICATIONS

International Search Report and Written Opinion for Application No. PCT/US2021/029139 dated Jul. 23, 2021.
Arseneault et al., Recent advances in click chemistry applied to dendrimer synthesis. Molecules. May 20, 2015;20(5):9263-94. doi: 10.3390/molecules20059263.
Artigas et al., The American-European Consensus Conference on ARDS, part 2. Ventilatory, pharmacologic, supportive therapy, study design strategies and issues related to recovery and remodeling. Intensive Care Med. Apr. 1998;24(4):378-98. doi: 10.1007/s001340050585.
Caminade et al., Dendrimers for drug delivery. J Mater Chem B. Jul. 14, 2014;2(26):4055-4066. doi: 10.1039/c4tb00171k. Epub Jun. 2, 2014.
Cao et al., A Trial of Lopinavir-Ritonavir in Adults Hospitalized with Severe Covid-19. N Engl J Med. May 7, 2020;382(19):1787-1799. doi: 10.1056/NEJMoa2001282. Epub Mar. 18, 2020.

(Continued)

*Primary Examiner* — Gyan Chandra
(74) *Attorney, Agent, or Firm* — Wolf, Greenfield & Sacks, P.C.

(57) ABSTRACT

A method for treating or preventing one or more symptoms of severe inflammation in the lung of a subject in need thereof includes administering to the subject a composition comprising dendrimers complexed, covalently conjugated, or intra-molecularly dispersed or encapsulated with one or more therapeutic or prophylactic agents, in an amount effective to treat, alleviate or prevent one or more symptoms of severe inflammation. The compositions and methods are useful for treating disorders characterized by cytokine storm, for example, for treating or preventing acute lung injury (ALI) and/or acute respiratory distress syndrome (ARDS) results in from ventilator use or infection such as with COVID-19, sepsis, and systemic bacterial infections in a subject in need thereof have been established. Preferably, the dendrimers are generation 4, 5, 6, 7, or 8 poly(amidoamine) (PAMAM) dendrimers, and the therapeutic agents are one or more anti-inflammatory and/or anti-oxidant agents such as N-acetyl cysteine.

29 Claims, 5 Drawing Sheets

(56) References Cited

OTHER PUBLICATIONS

Esfand et al., Poly(amidoamine) (PAMAM) dendrimers: from biomimicry to drug delivery and biomedical applications. Drug Discov Today. Apr. 1, 2001;6(8):427-436. doi: 10.1016/s1359-6446(01)01757-3.

Kannan et al., Emerging concepts in dendrimer-based nanomedicine: from design principles to clinical applications. J Intern Med. Dec. 2014;276(6):579-617. doi: 10.1111/joim.12280. Epub Jul. 31, 2014.

Lesniak et al., Biodistribution of fluorescently labeled PAMAM dendrimers in neonatal rabbits: effect of neuroinflammation. Mol Pharm. Dec. 2, 2013;10(12):4560-71. doi: 10.1021/mp400371r. Epub Oct. 30, 2013. Author manuscript.

McCray et al., Lethal infection of K18-hACE2 mice infected with severe acute respiratory syndrome coronavirus. J Virol. Jan. 2007;81(2):813-21. doi: 10.1128/JVI.02012-06. Epub Nov. 1, 2006.

Nance et al., Nanoscale effects in dendrimer-mediated targeting of neuroinflammation. Biomaterials. Sep. 2016;101:96-107. doi: 10.1016/j.biomaterials.2016.05.044. Epub May 26, 2016. Author manuscript.

Neal et al., Discovery and validation of a new class of small molecule Toll-like receptor 4 (TLR4) inhibitors. PLoS One. Jun. 12, 2013;8(6):e65779. doi: 10.1371/journal.pone.0065779.

Ruan et al., Clinical predictors of mortality due to COVID-19 based on an analysis of data of 150 patients from Wuhan, China. Intensive Care Med. May 2020;46(5):846-848. doi: 10.1007/s00134-020-05991-x. Epub Mar. 3, 2020. Erratum in: Intensive Care Med. Apr. 6, 2020.

Sharma et al., Combined A3 Coupling and Click Chemistry Approach for the Synthesis of Dendrimer-Based Biological Tools. ACS Macro Letters Oct. 2014; 3 (10), 1079-1083. DOI: 10.1021/mz5006298.

Sharma et al., Design and synthesis of multifunctional traceable dendrimers for visualizing drug delivery. RSC ADV., Apr. 2014; 4, 19242-19245.

Shi et al., COVID-19 infection: the perspectives on immune responses. Cell Death Differ. May 2020;27(5):1451-1454. doi: 10.1038/s41418-020-0530-3. Epub Mar. 23, 2020.

Tomalia et al., Dendrimers as multi-purpose nanodevices for oncology drug delivery and diagnostic imaging. Biochem Soc Trans. Feb. 2007;35(Pt 1):61-7. doi: 10.1042/BST0350061.

Yang et al., Clinical course and outcomes of critically ill patients with SARS-CoV-2 pneumonia in Wuban, China: a single-centered, retrospective, observational study. Lancet Respir Med. May 2020;8(5):475-481. doi: 10.1016/S2213-2600(20)30079-5. Epub Feb. 24, 2020. Erratum in: Lancet Respir Med. Apr. 2020;8(4):e26.

Zhou et al., Clinical course and risk factors for mortality of adult inpatients with COVID-19 in Wuhan, China: a retrospective cohort study. Lancet. Mar. 28, 2020;395(10229):1054-1062. doi: 10.1016/S0140-6736(20)30566-3. Epub Mar. 11, 2020. Erratum in: Lancet. Mar. 28, 2020;395(10229):1038. Erratum in: Lancet. Mar. 28, 2020;395(10229):1038.

International Search Report and Written Opinion for App. No. PCT/US2020/063332, dated Jul. 26, 2021.

International Preliminary Report on Patentability for App. No. PCT/US2020/063332, dated Jun. 16, 2022.

International Preliminary Report on Patentability for App. No. PCT/US2021/029139 dated Nov. 3, 2022.

International Search Report and Written Opinion for App. No. PCT/US2021/042097, dated Nov. 22, 2021.

International Preliminary Report on Patentability for App. No. PCT/US2021/042097, dated Jan. 26, 2023.

International Search Report and Written Opinion for App. No. PCT/US2020/063342, dated Mar. 16, 2021.

International Preliminary Report on Patentability for App. No. PCT/US2020/063342, dated Jun. 16, 2022.

Anders et al., Beyond tissue injury-damage-associated molecular patterns, toll-like receptors, and inflammasomes also drive regeneration and fibrosis. J Am Soc Nephrol. Jul. 2014;25(7):1387-400. doi: 10.1681/ASN.2014010117. Epub Apr. 24, 2014.

Ashton et al., Synthesis of Glycodendrimers by Modification of Poly(propylene imine) Dendrimers. Chem. Eur. J. Jun. 1997;3(6):974-84.

Bolisetty et al., Neutrophils in acute kidney injury: not neutral any more. Kidney Int. Apr. 2009;75(7):674-6. doi: 10.1038/ki.2008.689.

Boppana et al., Blockade of CXCR2 signalling: a potential therapeutic target for preventing neutrophil-mediated inflammatory diseases. Exp Biol Med (Maywood). May 2014;239(5):509-18. doi: 10.1177/1535370213520110. Epub Mar. 13, 2014.

Chen et al., Sterile inflammation: sensing and reacting to damage. Nat Rev Immunol. Dec. 2010;10(12):826-37. doi: 10.1038/nri2873. Epub Nov. 19, 2010. Author Manuscript, 35 pages.

Chen, PARP inhibitors: its role in treatment of cancer. Chin J Cancer. Jul. 2011;30(7):463-71. doi: 10.5732/cjc.011.10111.

Cleland et al., Abstract No. 0738. Systemic Administration of Novel Hydroxyl Dendrimers to Target Inflammation in Arthritic Tissues. ACR Convergence 2020 Conference. Nov. 7, 2020;72(suppl 10). 2 pages.

Cleland et al., Suppression of Murine Choroidal Neovascularization After Systemic Administration of a Targeted Anti-VEGF Therapy. ARVO Annual Meeting Abstract. Jun. 2020;61(7):3974. 2 pages.

Dolman et al., Dendrimer-Based Macromolecular Conjugate for the Kidney-Directed Delivery of a Multitargeted Sunitinib Analogue. Macromolecular Bioscience. Jan. 2012;12(1):93-103. Epub Oct. 13, 2011.

Elgogary et al., Combination therapy with BPTES nanoparticles and metformin targets the metabolic heterogeneity of pancreatic cancer. Proc Natl Acad Sci USA. Sep. 6, 2016;113(36):E5328-36. doi: 10.1073/pnas.1611406113. Epub Aug. 24, 2016.

Flood et al., STING pathway agonism as a cancer therapeutic. Immunol Rev. Jul. 2019;290(1):24-38.

Giarolla et al., Molecular modeling as a promising tool to study dendrimer prodrugs delivery. Journal of Molecular Structure: THEOCHEM. Jan. 15, 2010;939(1-3):133-8. Epub Oct. 1, 2009.

Gowda et al., A Metabolomics Study of BPTES Altered Metabolism in Human Breast Cancer Cell Lines. Front Mol Biosci. 2018;5:49. Epub May 15, 2018. 13 pages.

Haag et al., Targeting STING with covalent small-molecule inhibitors. Nature. Jul. 2018;559(7713):269-273. doi: 10.1038/s41586-018-0287-8. Epub Jul. 4, 2018.

Ham et al., Discovery, design and synthesis of Y-shaped peroxisome proliferator-activated receptor δ agonists as potent anti-obesity agents in vivo. Eur J Med Chem. Jul. 2012;53:190-202. doi: 10.1016/j.ejmech.2012.03.055. Epub Apr. 6, 2012.

Harney et al., The Selective Tie2 Inhibitor Rebastinib Blocks Recruitment and Function of Tie2 Hi Macrophages in Breast Cancer and Pancreatic Neuroendocrine Tumors. Mol Cancer Ther. Nov. 2017;16(11):2486-2501. doi: 10.1158/1535-7163.MCT-17-0241. Epub Aug. 24, 2017.

Hashemzaei et al., Anticancer and apoptosis-inducing effects of quercetin in vitro and in vivo. Oncology Reports. 2017;38:819-28. Epub Jun. 28, 2017.

Iacobazzi et al., Targeting human liver cancer cells with lactobionic acid-G(4)-PAMAM-FITC sorafenib loaded dendrimers. Int J Pharm. Aug. 7, 2017;528(1-2):485-497. doi: 10.1016/j.ijpharm.2017.06.049. Epub Jun. 15, 2017.

Jiang et al., SHP2 inhibitor specifically suppresses the stemness of KRAS-mutant non-small cell lung cancer cells. Artif Cells Nanomed Biotechnol. Dec. 2019;47(1):3231-3238. doi: 10.1080/21691401.2019.1646748.

Kim et al., Bifunctional compounds for targeted hepatic gene delivery. Gene Ther. Apr. 2007;14(8):704-8. doi: 10.1038/sj.gt.3302917. Epub Feb. 8, 2007.

Kurts et al., The immune system and kidney disease: basic concepts and clinical implications. Nat Rev Immunol. Oct. 2013;13(10):738-53. doi: 10.1038/nri3523. Epub Sep. 16, 2013.

Kuruvilla et al., Dendrimer-doxorubicin conjugates exhibit improved anticancer activity and reduce doxorubicin-induced cardiotoxicity in a murine hepatocellular carcinoma model. PLoS One. Aug. 22, 2017;12(8):e0181944. doi: 10.1371/journal.pone.0181944. eCollection 2017. 24 pages.

(56) References Cited

OTHER PUBLICATIONS

Kuruvilla et al., Effect of N-acetylgalactosamine ligand valency on targeting dendrimers to hepatic cancer cells. Int J Pharm. Jul. 1, 20180;545(1-2):27-36. doi: 10.1016/j.ijpharm.2018.04.028. Epub Apr. 16, 2018.

Kuruvilla et al., N-Acetylgalactosamine-Targeted Delivery of Dendrimer-Doxorubicin Conjugates Influences Doxorubicin Cytotoxicity and Metabolic Profile in Hepatic Cancer Cells. Advanced Healthcare Materials. Jan. 2017;6(5):1601046. 15 pages.

Lee et al., Hyaluronate—Death Receptor 5 Antibody Conjugates for Targeted Treatment of Liver Metastasis. Biomacromolecules. 2016;17(9):3085-93. Author manuscript provided. Epub Aug. 12, 2016. 30 pages.

Li et al., Activation of the Proapoptotic Death Receptor DR5 by Oligomeric Peptide and Antibody Agonists. J. Mol. Biol. 2006;361:522-36. Epub Jul. 7, 2006.

Li et al., Bioinspired intrafibrillar mineralization of human dentine by PAMAM dendrimer. Biomaterials. Sep. 2013;34(28):6738-47. doi: 10.1016/j.biomaterials.2013.05.046. Epub Jun. 17, 2013.

Liaw et al., EXTH-40. Specific Dendrimer-Mediated Delivery of Immunotherapy BLZ945 to Tumor-Associated Macrophages Improves Therapeutic Efficacy in Glioblastoma. Neuro Oncol. Nov. 2019; 21(Suppl 6): vi90. Epub Nov. 11, 2019.

Liu et al., The Role of PPAR-δ in Metabolism, Inflammation, and Cancer: Many Characters of a Critical Transcription Factor. Int J Mol Sci. Oct. 26, 2018;19(11):3339. doi: 10.3390/ijms19113339.

Luke et al., The biology and clinical development of MEK inhibitors for cancer. Drugs. Dec. 2014;74(18):2111-28. doi: 10.1007/s40265-014-0315-4.

Lv et al., Inhibiting Solid Tumor Growth In Vivo by Non-Tumor-Penetrating Nanomedicine. Small. Mar. 2017;13(12). doi: 10.1002/smll.201600954. Epub Jan. 12, 2017. 10 pages.

Madaan et al., Evaluation of polyamidoamine dendrimers as potential carriers for quercetin, a versatile flavonoid. Drug Deliv. 2016;23(1):254-62. doi: 10.3109/10717544.2014.910564. Epub May 20, 2014.

Matsuura et al., L-Cysteine and L-Serine Modified Dendrimer with Multiple Reduced Thiols as a Kidney-Targeting Reactive Oxygen Species Scavenger to Prevent Renal Ischemia/Reperfusion Injury. Pharmaceutics. Dec. 1, 2018;10(4):251. doi: 10.3390/pharmaceutics10040251.

Medina et al., Enzyme-activated nanoconjugates for tunable release of doxorubicin in hepatic cancer cells. Biomaterials. Jun. 1, 2013;34(19):4655-66.

Medina et al., N-acetylgalactosamine-functionalized dendrimers as hepatic cancer cell-targeted carriers. Biomaterials. Jun. 2011;32(17):4118-29. doi: 10.1016/j.biomaterials.2010.11.068. Epub Mar. 22, 2011. Author manuscript provided. 25 pages.

Medina et al., Targeting hepatic cancer cells with pegylated dendrimers displaying N-acetylgalactosamine and SP94 peptide ligands. Adv Healthc Mater. Oct. 2013;2(10):1337-50. doi: 10.1002/adhm.201200406. Epub Apr. 3, 2013.

Medzhitov et al., Inflammation 2010: new adventures of an old flame. Cell. Mar. 19, 2010;140(6):771-6. doi: 10.1016/j.cell.2010.03.006.

Miret et al., Suppression of Myeloid Cell Arginase Activity leads to Therapeutic Response in a NSCLC Mouse Model by Activating Anti-Tumor Immunity. J Immunother Cancer. Feb. 6, 2019;7(1):32. doi: 10.1186/s40425-019-0504-5. 12 pages.

Mizrachi et al., Tumour-specific PI3K inhibition via nanoparticle-targeted delivery in head and neck squamous cell carcinoma. Nature Communications. 2017;8:14292. Epub Feb. 13, 2017. 10 pages.

Mullins et al., Intratumoral immunotherapy with TLR7/8 agonist MEDI9197 modulates the tumor microenvironment leading to enhanced activity when combined with other immunotherapies. Journal for Immunotherapy of Cancer. Sep. 11, 2019;7(1):244. 18 pages.

Porterfield et al., (575g) Sugar-Guided Organ and Cellular Targeting of PAMAM Dendrimers. 2018 AIChE Annual Meeting. Pittsburgh, PA. Oct. 31, 2018. 5 pages.

Porterfield et al., (675c) Galactosylated Dendrimer Targets Hepatocytes and Improves Therapeutic Outcomes in a Severe Model of Acetaminophen Poisoning. 2019 AIChE Annual Meeting. Orlando, FL. Nov. 14, 2019. 4 pages.

Porterfield et al., 392a—Graduate Student Award Session: Galactosylated Dendrimer Targets Hepatocytes and Improves Therapeutic Outcomes in a Severe Model of Acetaminophen Poisoning. 2019 AIChE Annual Meeting. Orlando, FL. Nov. 14, 2019. 5 pages.

Ramesh et al., CSF1R- and SHP2-Inhibitor-Loaded Nanoparticles Enhance Cytotoxic Activity and Phagocytosis in Tumor-Associated Macrophages. Advanced Materials. 2019;31:1904364. 11 pages.

Ren et al., Quercetin nanoparticles display antitumor activity via proliferation inhibition and apoptosis induction in liver cancer cells. Int J Oncol. Apr. 2017;50(4):1299-1311. doi: 10.3892/ijo.2017.3886. Epub Feb. 20, 2017.

Rodell et al., TLR7/8-agonist-loaded nanoparticles promote the polarization of tumour-associated macrophages to enhance cancer immunotherapy. Nat Biomed Eng. Aug. 2018;2(8):578-588. doi: 10.1038/s41551-018-0236-8. Epub May 21, 2018.

Rudolph et al., Indanylacetic acid derivatives carrying 4-thiazolyl-phenoxy tail groups, a new class of potent PPAR alpha/gamma/delta pan agonists: synthesis, structure-activity relationship, and in vivo efficacy. J Med Chem. Mar. 8, 2007;50(5):984-1000. doi: 10.1021/jm061299k. Epub Feb. 3, 2007.

Shafie et al., Sorafenib-loaded PAMAM dendrimer attenuates liver fibrosis and its complications in bile-duct-ligated rats. Canadian Journal of Physiology and Pharmacology. May 2019;97(8):691-8.

Sharma et al., Effect of mannose targeting of hydroxyl PAMAM dendrimers on cellular and organ biodistribution in a neonatal brain injury model. J Control Release. Aug. 10, 2018;283:175-89. doi: 10.1016/j.jconrel.2018.06.003. Epub Jun. 5, 2018.

She et al., PEGylated Dendrimer-Doxorubicin Cojugates as pH-Sensitive Drug Delivery Systems: Synthesis and In Vitro Characterization. J Biomed Nanotechnol. Jun. 2015;11(6):964-78. doi: 10.1166/jbn.2015.1865.

Shetab et al., TLR4-Based Immunotherapeutics in Cancer: A Review of the Achievements and Shortcomings. Mol Pharm. Nov. 5, 2018;15(11):4777-4800. doi: 10.1021/acs.molpharmaceut.8b00691. Epub Oct. 3, 2018.

Steele et al., CXCR2 Inhibition Profoundly Suppresses Metastases and Augments Immunotherapy in Pancreatic Ductal Adenocarcinoma. Cancer Cell. Jun. 13, 2016;29(6): 832-845.

Su et al., STING activation in cancer immunotherapy. Theranostics. 2019; 9(25):7759-7771. Epub Oct. 15, 2019.

Sung et al., Combined delivery of sorafenib and a MEK inhibitor using CXCR4-targeted nanoparticles reduces hepatic fibrosis and prevents tumor development. Theranostics. Jan. 1, 2018;8(4):894-905. doi: 10.7150/thno.21168. eCollection 2018.

Vallés et al., Acute kidney injury: what part do toll-like receptors play? Int J Nephrol Renovasc Dis. Jun. 19, 2014;7:241-51. doi: 10.2147/IJNRD.S37891.

Van De Ven et al., Nanoformulation of Olaparib Amplifies PARP Inhibition and Sensitizes PTEN/TP53-Deficient Prostate Cancer to Radiation. Molecular Cancer Therapeutics. Jul. 2017;16(7):1279-89.

Van Rompaey et al., Preclinical Characterization of GLPG0634, a Selective Inhibitor of JAK1, for the Treatment of Inflammatory Diseases. J Immunol. Oct. 1, 2013;191(7):3568-3577. Epub Sep. 4, 2013.

Wang et al., Disulfide bond-disrupting agents activate the tumor necrosis family-related apoptosis-inducing ligand/death receptor 5 pathway. Cell Death Discovery. Dec. 10, 2019;5:153. 15 pages.

Wang et al., Small-molecule activation of the TRAIL receptor DR5 in human cancer cells. Nat Chem Biol. Feb. 2013;9(2):84-9. doi: 10.1038/nchembio.1153. Epub Dec. 23, 2012.

Wu et al., Hydroxyapatite-anchored dendrimer for in situ remineralization of human tooth enamel. Biomaterials. Jul. 2013;34(21):5036-47. doi: 10.1016/j.biomaterials.2013.03.053. Epub Apr. 8, 2013.

Yamashita et al., Bone-targeting dendrimer for the delivery of methotrexate and treatment of bone metastasis. Journal of Drug Targeting. 2018;26(9):818-28. Epub Jan. 29, 2018. Abstract Only.

(56) References Cited

OTHER PUBLICATIONS

Yang et al., Targeting PI3K in cancer: mechanisms and advances in clinical trials. Molecular Cancer. Molecular Cancer. 2019;18:26. 28 pages.

Yousef et al., Development of asialoglycoprotein receptor directed nanoparticles for selective delivery of curcumin derivative to hepatocellular carcinoma. Heliyon. Dec. 22, 2018;4(12):e01071. doi: 10.1016/j.heliyon.2018.e01071. 26 pages.

Zhang et al., A nano-liposome formulation of the PARP inhibitor Talazoparib enhances treatment efficacy and modulates immune cell populations in mammary tumors of BRCA-deficient mice. Theranostics. 2019; 9(21): 6224-6238. Epub Aug. 14, 2019.

\* cited by examiner

METHODS OF TREATING SEVERE INFLAMMATION

CROSS REFERENCE TO RELATED APPLICATIONS

This application claims priority to and benefit of U.S. Provisional Application No. 63/015,131 filed on Apr. 24, 2020, the disclosure of which is hereby incorporated herein by reference in its entirety.

FIELD OF THE INVENTION

The invention is generally in the field of drug delivery, and in particular, a method of delivering drugs bound via dendrimer formulations selectively to sites or regions of inflammation in patients with respiratory distress.

BACKGROUND OF THE INVENTION

The coronavirus disease 2019 (COVID-19) outbreak that started in Wuhan, Hubei province, China in December 2019 extended across the globe with more than 1.5 million confirmed cases and at least 94,000 deaths reported in 184 countries as of Apr. 9, 2020, and over 140 million confirmed cases and over three million deaths as of April 2021. COVID-19 is caused by a previously unknown coronavirus, named Severe Acute Respiratory Syndrome Coronavirus 2 (SARS-CoV-2).

SARS-CoV-2 causes pneumonia having a wide range of presentation, from very mild to critically ill. A single center study from Wuhan characterizing the outcomes of critically ill SARS-CoV-2 patients indicated that the mortality rate amongst patients who required care within an intensive care unit (ICU) was high (61.5%), and the median duration from ICU time to death was 7 days for non-survivors. Non-survivors were more likely to develop acute respiratory distress syndrome (ARDS) (81% of non-survivors) (Yang X, et al., The Lancet Respiratory Medicine, 2213-2600, (2020)). In a larger cohort of patients from Wuhan, 98% of non-survivors had ARDS, compared to 36% of survivors, and 70% of non-survivors had septic shock, indicating systemic inflammation compared to 0% of survivors (Zhou, et al., Lancet, 395: 1054-62 (2020)). Increase in cytokines such as IL-6 was observed in these patients, with a subgroup of patients developing cytokine storm (Ruan, et al., Intensive Care Med.; online Mar. 3, 2020). Therapeutic strategies have been mostly supportive, with mixed results seen in patients receiving anti-inflammatory agents such as corticosteroids, and no benefit observed with the anti-viral combination of lopinavir-ritonavir (Cao, et al., N Engl J Med, (2020)).

In patients with severe COVID-19, two-phases of immune response appear to be involved. The initial protective adaptive immune response is necessary to eliminate the virus. However, when the protective immune response is impaired, there is massive destruction of the affected tissues and further viral propagation. These damaged cells then induce inflammation in the lungs that is primarily mediated by pro-inflammatory macrophages and granulocytes (Shi, et al., Cell Death & Differentiation (2020)). Both oxidative stress and inflammation play a major role in the pathophysiology of ARDS (Reddy, Antioxidants & Redox Signaling, 2003-2012 (2007)). Activated macrophages play a central role in mediating the pathophysiology of ARDS, and shifting the phenotype of the macrophages from a pro-inflammatory (M1-like) to a 'normal' or an anti-inflammatory (M2-like) phenotype may be highly beneficial for ARDS outcome.

Systemic inflammation and the associated cytokine storm are also mediated by pro-inflammatory macrophages. Therefore, it is an object of the invention to provide compositions and methods for reducing or preventing inflammation in the lungs, and/or systemic inflammation resulting from COVID-19 induced pneumonia.

It is also an object of the invention to provide compositions that reduce or prevent the pathological processes associated with the development and progression of acute respiratory distress syndrome, and methods of making and using thereof.

It is yet another object of the invention to provide compositions and methods for selectively targeting active agents to pro-inflammatory cells at the site of inflammation in the lungs associated with acute respiratory distress syndrome.

SUMMARY OF THE INVENTION

A method for treating or preventing one or more symptoms of severe inflammation in an organ of a human in need thereof includes administering to the human dendrimers complexed, covalently conjugated, or intra-molecularly dispersed or encapsulated with one or more therapeutic or prophylactic agents, in an amount effective to treat, alleviate or prevent one or more symptoms of severe inflammation. As used herein, severe inflammation is defined by over-reactive M1 macrophages and/or elevations in proinflammatory markers (IL-6, CRP, ferritin, IL-1b, etc.), which result in a chronically elevated response. The compositions and methods are useful for treating disorders characterized by cytokine storm, for example, for treating or preventing acute lung injury (ALI) and/or acute respiratory distress syndrome (ARDS) resulting from ventilator use or infection such as with COVID-19, sepsis, and systemic bacterial infections in a subject in need thereof have been established.

Methods of treating a subject with ALI and/or ARDS include administering to the subject dendrimers complexed to, covalently conjugated, or intra-molecularly dispersed or encapsulated with one or more therapeutic or prophylactic agents, in an amount effective to treat, alleviate or prevent one or more symptoms of acute lung injury or acute respiratory distress syndrome. Exemplary acute lung injuries include ventilator-induced lung injury and gastric aspiration-induced lung injury. An exemplary cause for acute respiratory distress syndrome includes infection with a virus, such as the SARS-COVID-2 virus. Therefore, the compositions and methods are suitable for treating or preventing symptoms of ALI and/or ARDS caused by SARS-COVID-2 virus.

In some embodiments, the dendrimers are hydroxyl-terminated dendrimers, such as a generation 4, generation 5, or generation 6 poly(amidoamine) (PAMAM) dendrimers. In some embodiments, one or more therapeutic agent is an anti-inflammatory agent. An exemplary therapeutic agent is N-acetyl cysteine.

The dendrimer compositions are administered in an amount effective to reduce inflammation in the lung, for example, to reduce vascular leakage or vascular permeability in the lung, increase alveolar cell integrity or endothelial cell integrity in the lung, increase the ratio of arterial oxygen to the fraction of inspired oxygen ($PaO_2/FiO_2$), and/or reduce bronchoalveolar lavage (BAL) protein levels or bronchoalveolar lavage cell count. In some embodiments, the methods administer dendrimer compositions in an amount effective to reduce one or more pro-inflammatory cells, chemokines, and/or cytokines in the lung, for example, to reduce one or more pro-inflammatory chemokines selected from MCP-1, CXCL-8, CXCL-1, CXCL-5, and CCL-2, or one or more pro-inflammatory cytokines selected from the C-reactive protein (CRP), ferritin, IL-6, TNF-α, IL-12, IL-1β, and IL-18, or pro-inflammatory cells such as M1-like macrophages.

The dendrimer compositions are formulated for intravenous, subcutaneous, or intramuscular administration, or pulmonary administration and are administered via the intravenous, subcutaneous, or intramuscular route by injection or catheter, or via the nasal or pulmonary route. In some embodiments, the composition is administered prior to, in conjunction with, subsequent to, or in alternation with treatment with one or more additional therapies or procedures. Exemplary additional therapeutic agents which can be administered as part of the formulation or co-administered with dendrimer-drug, include antimicrobials, surfactant, and anti-inflammatories such as corticosteroids. Exemplary additional procedures include prone positioning, recruitment maneuver, inhalation of NO, extracorporeal membrane oxygenation (ECMO), intubation, and/or inhalation of $PGI_2$.

Pharmaceutical compositions for use in treating or preventing acute lung injury (ALI) and/or acute respiratory distress syndrome (ARDS) in a subject in need thereof are also provided.

Kits include a packaging containing one or more single unit dose of a composition including dendrimers covalently conjugated with one or more anti-inflammatory agents, and instructions on how the dose is to be administered for treatment of acute lung injury.

DETAILED DESCRIPTION OF THE INVENTION

I. Definitions

Figure 1:
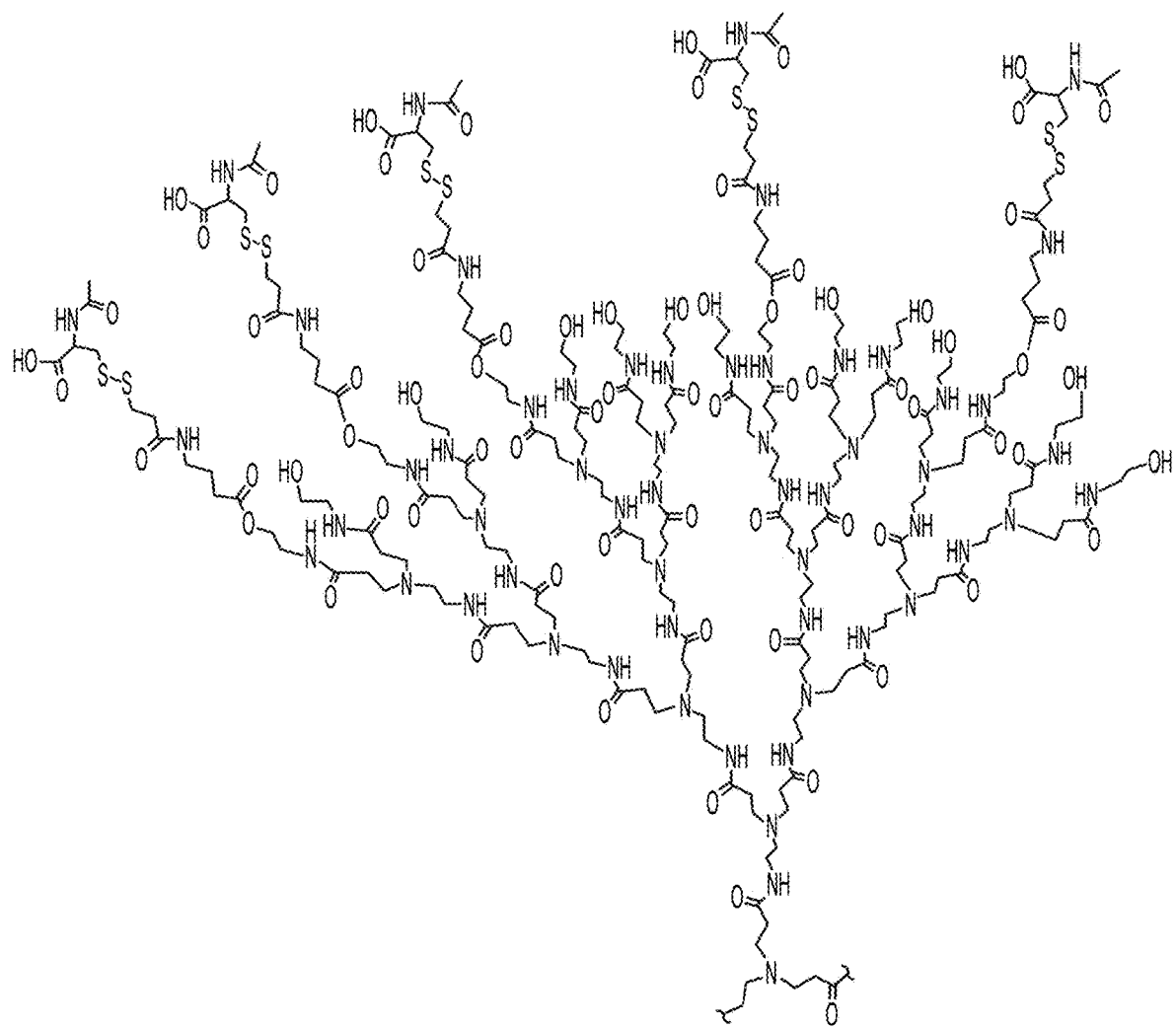
FIG. 1 is a representative chemical structure of N-acetyl cysteine conjugated to a G4-OH poly(amidoamine) or PAMAM dendrimer. PAMAM dendrimer is made of repetitive branching units of methyl acrylate and ethylene diamine. When 20 NAC units are present, the overall formula is $C_{862}H_{1544}N_{226}O_{288}S_{40}$, with an average molecular weight of 20,965 Da.
Figure 1:
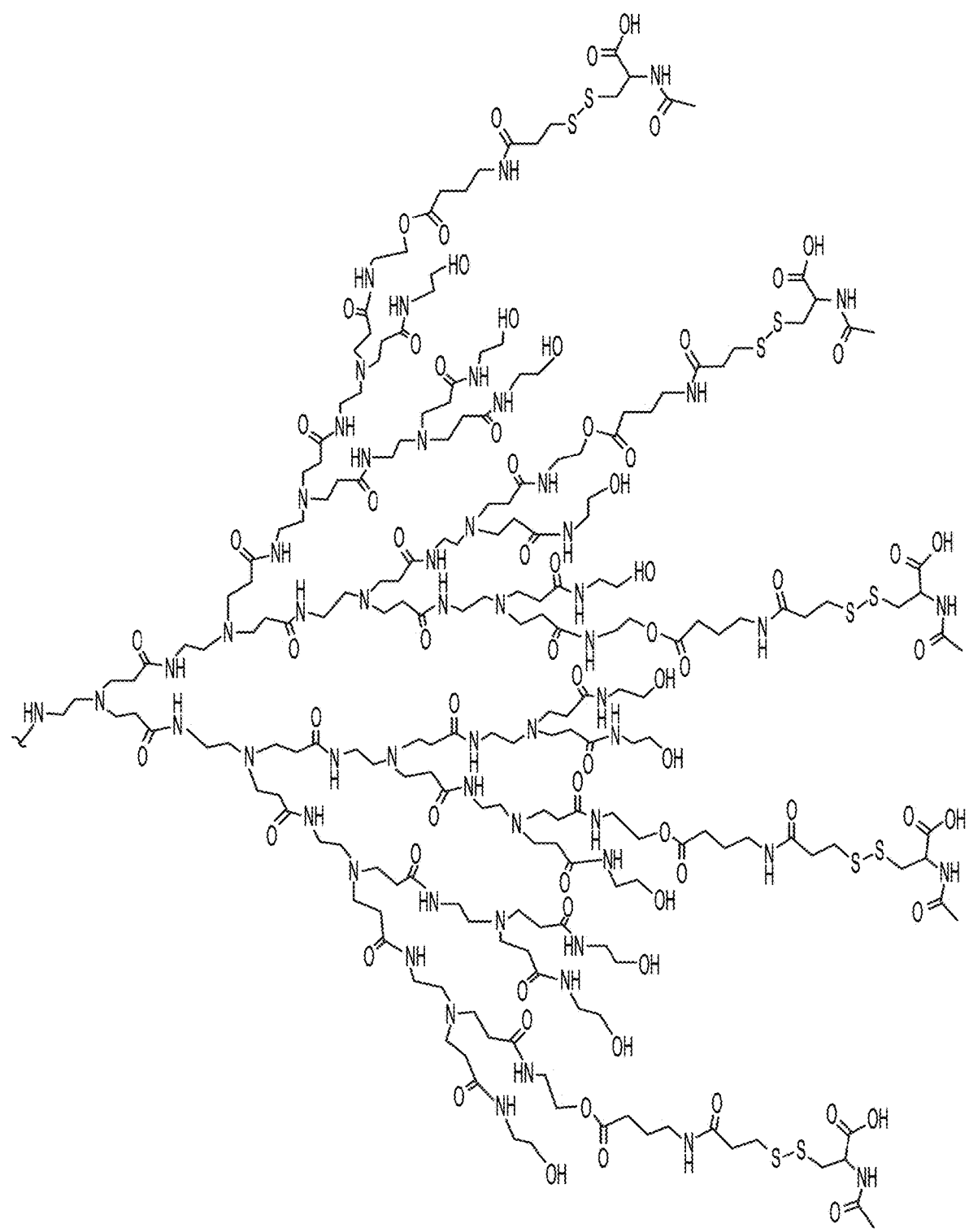
Figure 1:
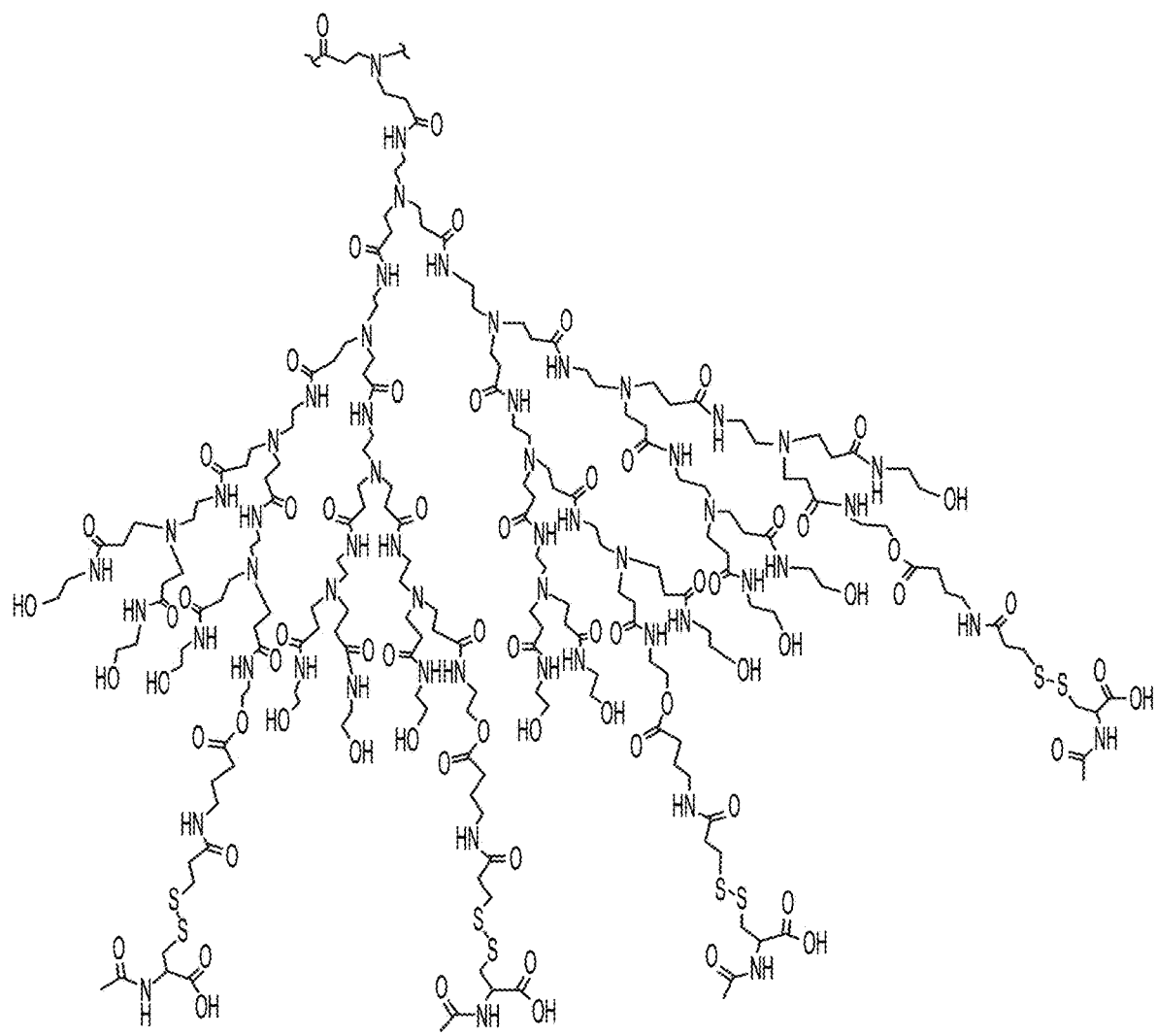
Figure 1:
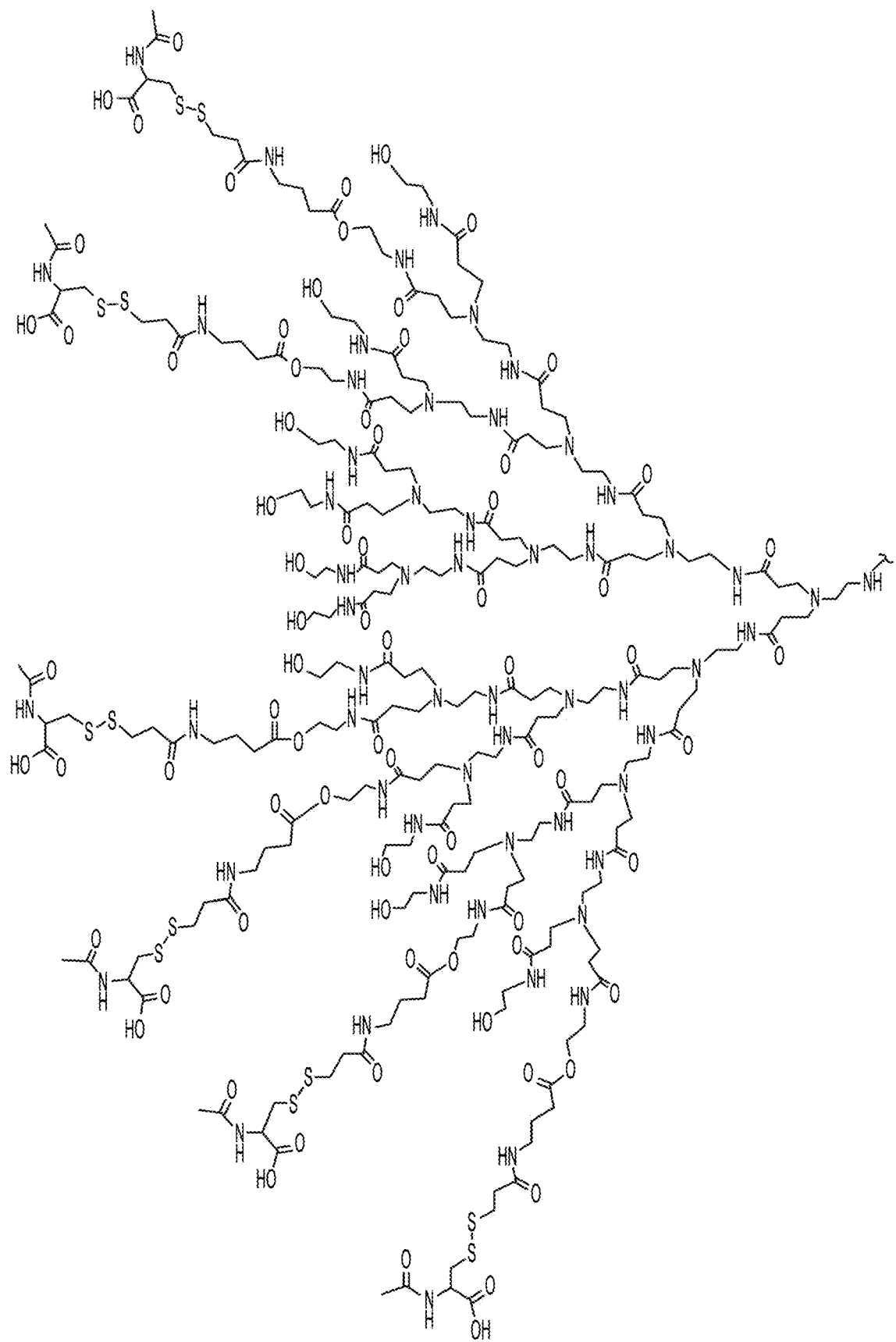

The terms "active agent" or "biologically active agent" refer to therapeutic, prophylactic or diagnostic agents which are chemical or biological compounds that induce a desired pharmacological and/or physiological effect, which may be prophylactic, therapeutic or diagnostic. These may be a nucleic acid, a nucleic acid analog, a small molecule having a molecular weight less than 2 kDa, more typically less than 1 kDa, a peptidomimetic, a protein or peptide, carbohydrate or sugar, lipid, or a combination thereof. The terms also encompass pharmaceutically acceptable, pharmacologically active derivatives of active agents, including, but not limited to, salts, esters, amides, prodrugs, active metabolites, and analogs.

The term "pharmaceutically acceptable salts" is art-recognized, and includes relatively non-toxic, inorganic and organic acid addition salts of compounds. Examples of pharmaceutically acceptable salts include those derived from mineral acids, such as hydrochloric acid and sulfuric acid, and those derived from organic acids, such as ethanesulfonic acid, benzenesulfonic acid, and p-toluenesulfonic acid. Examples of suitable inorganic bases for the formation of salts include the hydroxides, carbonates, and bicarbonates of ammonia, sodium, lithium, potassium, calcium, magnesium, aluminum, and zinc. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine;

The term "therapeutic agent" refers to an active agent that can be administered to treat one or more symptoms of a disease or disorder.

The term "diagnostic agent" generally refers to an active agent that can be administered to reveal, pinpoint, and define the localization of a pathological process. The diagnostic agents can label target cells that allow subsequent detection or imaging of these labeled target cells.

The term "prophylactic agent" generally refers to an active agent that can be administered to prevent disease or to prevent certain conditions.

The phrase "pharmaceutically acceptable" or "biocompatible" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

The term "therapeutically effective amount" refers to an amount of the therapeutic agent that, when incorporated into and/or onto dendrimers, produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation. In some embodiments, the term "effective amount" refers to an amount of a prophylactic agent or therapeutic agent to reduce or diminish the risk of developing acute lung injury or to reduce or diminish the symptoms of one or more lung diseases or disorders, such as reducing inflammation in the lung. Additional desired results also include reducing vascular leakage or vascular permeability in the lung, increasing alveolar cell integrity or increasing endothelial cell integrity in the lung, reducing bronchoalveolar lavage (BAL) protein levels or BAL cell count.

The terms "inhibit" or "reduce" in the context of inhibition, mean to reduce or decrease in activity and quantity. This can be a complete inhibition or reduction in activity or quantity, or a partial inhibition or reduction. Inhibition or reduction can be compared to a control or to a standard level. Inhibition can be 5, 10, 25, 50, 75, 80, 85, 90, 95, 99, or 100%. For example, dendrimer compositions including one or more agents may inhibit or reduce the activity and/or quantity of pro-inflammatory (M1-like) macrophages, and/or pro-inflammatory cytokines in a diseased lung by about 10%, 20%, 30%, 40%, 50%, 75%, 85%, 90%, 95%, or 99% from the activity and/or quantity of the same cells in the lung of subjects that did not receive, or were not treated with the dendrimer compositions. In some embodiments, the inhibition and reduction are compared at mRNAs, proteins, cells, tissues and organs levels.

The term "treating" or "preventing" a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain. Desirable effects of treatment include decreasing the rate of disease progression, ameliorating or palliating the disease state, and remission or improved prognosis. For example, an individual is successfully "treated" if one or more symptoms associated with ARDS are mitigated or eliminated, including, but are not limited to, reducing vascular leakage or vascular permeability in the lung, increasing alveolar cell integrity or increasing endothelial cell integrity in the lung, increasing the quality of life of those suffering from the disease, decreasing the dose of other medications required to treat the disease, delaying the progression of the disease, and/or prolonging survival of individuals.

The term "biodegradable" generally refers to a material that will degrade or erode under physiologic conditions to smaller units or chemical species that are capable of being metabolized, eliminated, or excreted by the subject. The degradation time is a function of composition and morphology.

The term "dendrimer" includes, but is not limited to, a molecular architecture with an interior core, interior layers (or "generations") of repeating units regularly attached to this initiator core, and an exterior surface of terminal groups attached to the outermost generation.

"Functionalize" means to modify a compound or molecule in a manner that results in the attachment of a functional group or moiety. For example, a molecule may be functionalized by the introduction of a molecule which makes the molecule a strong nucleophile or strong electrophile.

The term "targeting moiety" refers to a moiety that localizes to or away from a specific locale. The moiety may be, for example, a protein, nucleic acid, nucleic acid analog, carbohydrate, or small molecule. The entity may be, for example, a therapeutic compound such as a small molecule, or a diagnostic entity such as a detectable label. The locale may be a tissue, a particular cell type, or a subcellular compartment. In one embodiment, the targeting moiety directs the localization of an active agent.

The term "prolonged residence time" refers to an increase in the time required for an agent to be cleared from a patient's body, or organ or tissue of that patient. In certain embodiments, "prolonged residence time" refers to an agent that is cleared with a half-life that is 10%, 20%, 50% or 75% longer than a standard of comparison such as a comparable agent without conjugation to a delivery vehicle such as a dendrimer. In certain embodiments, "prolonged residence time" refers to an agent that is cleared with a half-life of 2, 5, 10, 20, 50, 100, 200, or 10000 times longer than a standard of comparison such as a comparable agent without a dendrimer that specifically target specific cell types associated with the site of inflammation.

The terms "incorporated" and "encapsulated" refer to incorporating, formulating, or otherwise including an active agent into and/or onto a composition that allows for release, such as sustained release, of such agent in the desired application. The active agent or other material can be incorporated into a dendrimer, including to one or more surface functional groups of such dendrimer (by covalent, ionic, or other binding interaction), physical admixture, enveloping the agent within the dendritic structure, encapsulated inside the dendritic structure, etc.

II. Compositions

Dendrimer complexes and conjugates suitable for delivering one or more active agent, particularly one or more active agents to prevent, treat or diagnose acute lung injury (ALI) and acute respiratory distress syndrome (ARDS), particularly those associated with infection, trauma, radiation, and other environmental or medical treatment-associated insults to the lung are described. The compositions are particularly suited for treating ARDS and/or systemic inflammation caused by a pathogenic viral infection, including diseases caused by coronavirus infection, such as COVID-19.

Compositions of dendrimer complexes and conjugates including one or more prophylactic, therapeutic, and/or diagnostic agents encapsulated, associated, and/or conjugated in the dendrimers are also provided. Generally, one or more active agents are encapsulated, associated, and/or conjugated in the dendrimer complex at a concentration of about 0.01% to about 30% by weight, preferably about 1% to about 20% by weight, more preferably about 5% to about 20% by weight or about 10% to about 20% by weight. Preferably, an active agent is covalently conjugated to the dendrimer via one or more linkages such as disulfide, ester, ether, thioester, carbamate, carbonate, hydrazine, and amide, optionally via one or more spacers. In some embodiments, the spacer is an active agent, such as N-acetyl cysteine. Exemplary active agents include anti-inflammatory drugs, vasodilators, and anti-infective agents.

In preferred embodiments, the dendrimer-active agent composition includes a hydroxylated poly(amidoamine), or PAMAM dendrimer which is made of repetitive reactions of methyl acrylate and ethylene diamine. In a particular embodiment, a generation-4 hydroxyl-terminated PAMAM dendrimers containing an ethylene diamine (EDA) core, amidoamine repeat units ([$CH_2CH_2CONHCH_2CH_2N$]), and 64 hydroxyl end groups (chemical formula: $C_{622}H_{1184}N_{186}O_{188}$) with approximately 20 of the 64 hydroxyls subsequently converted to amine groups and then to a thiol group, for eventual conjugation with the active component, N-acetyl cysteine (NAC), using a disulfide bond (as shown in Structure I and in FIG. 1). When 20 NAC units are present the overall formula is $C_{862}H_{1544}N_{226}O_{288}S_{40}$, with an average molecular weight of 20,965 Da. NAC represents approximately 16% of the total mass of the molecule.

Structure I

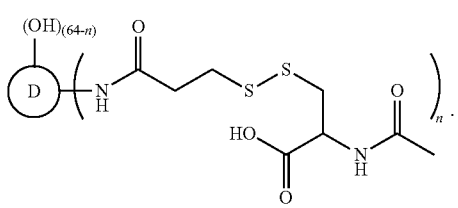

wherein D is preferably a generation-4 hydroxyl-terminated PAMAM dendrimers containing an ethylene diamine (EDA) core, amidoamine repeat units ([$CH_2CH_2$ $CONHCH_2CH_2N$]) and 64 hydroxyl end groups (chemical formula: $C_{622}H_{1184}N_{186}O_{188}$) prior to conjugation to any active agents, and wherein n=15-25, preferably about 20.

The presence of the additional agents can affect the zeta-potential or the surface charge of the particle. In one embodiment, the zeta potential of the dendrimers is between −100 mV and 100 mV, between −50 mV and 50 mV, between −25 mV and 25 mV, between −20 mV and 20 mV, between −10 mV and 10 mV, between −10 mV and 5 mV, between −5 mV and 5 mV, or between −2 mV and 2 mV. The range above is inclusive of all values from −100 mV to 100 mV. In a preferred embodiment, the surface charge is neutral or near-neutral, i.e., between −10 mV and 10 mV, between −5 mV and 5 mV, or between −2 mV and 2 mV. Dendrimers having a generation-4 hydroxyl-terminated PAMAM dendrimers and about 18-22 NAC units conjugated thereto have a particle size of approximately 5 nm and a zeta potential of approximately 7 mV.

A. Dendrimers

Dendrimers are three-dimensional, hyperbranched, monodispersed, globular and polyvalent macromolecules including a high density of surface end groups (Tomalia, D. A., et al., Biochemical Society Transactions, 35, 61 (2007); and Sharma, A., et al., ACS Macro Letters, 3, 1079 (2014)). Due to their unique structural and physical features, dendrimers are useful as nano-carriers for various biomedical applications including targeted drug/gene delivery, imaging and diagnosis (Sharma, A., et al., RSC Advances, 4, 19242 (2014); Caminade, A.-M., et al., Journal of Materials Chemistry B, 2, 4055 (2014); Esfand, R., et al., Drug Discovery Today, 6, 427 (2001); and Kannan, R. M., et al., Journal of Internal Medicine, 276, 579 (2014)).

Recent studies have shown that dendrimer surface groups have a significant impact on their biodistribution (Nance, E., et al., Biomaterials, 101, 96 (2016)). Hydroxyl terminated generation 4 PAMAM dendrimers (~4 nm size) without any targeting ligand cross the impaired BBB upon systemic administration in a rabbit model of cerebral palsy (CP) significantly more (>20 fold) as compared to healthy controls, and selectively target activated microglia and astrocytes (Lesniak, W. G., et al., Mol Pharm, 10 (2013)).

The term "dendrimer" includes, but is not limited to, a molecular architecture with an interior core and layers (or "generations") of repeating units which are attached to and extend from this interior core, each layer having one or more branching points, and an exterior surface of terminal groups attached to the outermost generation. In some embodiments, dendrimers have regular dendrimeric or "starburst" molecular structures.

Generally, dendrimers have a diameter between about 1 nm and about 50 nm, more preferably between about 1 nm and about 20 nm, between about 1 nm and about 10 nm, or between about 1 nm and about 5 nm. In some embodiments, the diameter is between about 1 nm and about 2 nm. Conjugates are generally in the same size range, although large proteins such as antibodies may increase the size by 5-15 nm. In general, agent is encapsulated in a ratio of agent to dendrimer of between 1:1 and 4:1 for the larger generation dendrimers. In preferred embodiments, the dendrimers have a diameter effective to penetrate lung epithelial tissue and to retain in target cells for a prolonged period.

In some embodiments, dendrimers have a molecular weight between about 500 Daltons and about 100,000 Daltons, preferably between about 500 Daltons and about 50,000 Daltons, most preferably between about 1,000 Daltons and about 20,000 Dalton.

Suitable dendrimers scaffolds that can be used include poly(amidoamine), also known as PAMAM, or STARBURST™ dendrimers; polypropylamine (POPAM), polyethylenimine, polylysine, polyester, iptycene, aliphatic poly (ether), and/or aromatic polyether dendrimers. The dendrimers can have carboxylic, amine and/or hydroxyl terminations. In preferred embodiments, the dendrimers have hydroxyl terminations. Each dendrimer of the dendrimer complex may be same or of similar or different chemical nature than the other dendrimers (e.g., the first dendrimer may include a PAMAM dendrimer, while the second dendrimer may be a POPAM dendrimer).

The term "PAMAM dendrimer" means poly(amidoamine) dendrimer, which may contain different cores, with amidoamine building blocks, and can have carboxylic, amine and hydroxyl terminations of any generation including, but not limited to, generation 1 PAMAM dendrimers, generation 2 PAMAM dendrimers, generation 3 PAMAM dendrimers, generation 4 PAMAM dendrimers, generation 5 PAMAM dendrimers, generation 6 PAMAM dendrimers, generation 7 PAMAM dendrimers, generation 8 PAMAM dendrimers, generation 9 PAMAM dendrimers, or generation 10 PAMAM dendrimers. In the preferred embodiment, the dendrimers are soluble in the formulation and are generation ("G") 4, 5 or 6 dendrimers. The dendrimers may have hydroxyl groups attached to their functional surface groups.

Methods for making dendrimers are known to those of skill in the art and generally involve a two-step iterative reaction sequence that produces concentric shells (generations) of dendritic β-alanine units around a central initiator core (e.g., ethylenediamine-cores). Each subsequent growth step represents a new "generation" of polymer with a larger molecular diameter, twice the number of reactive surface sites, and approximately double the molecular weight of the preceding generation. Dendrimer scaffolds suitable for use are commercially available in a variety of generations. Preferable, the dendrimer compositions are based on generation 0, 1, 2, 3, 4, 5, 6, 7, 8, 9, or 10 dendrimeric scaffolds. Such scaffolds have, respectively, 4, 8, 16, 32, 64, 128, 256, 512, 1024, 2048, and 4096 reactive sites. Thus, the dendrimeric compounds based on these scaffolds can have up to the corresponding number of combined targeting moieties, if any, and active agents.

In some embodiments, the dendrimers include a plurality of hydroxyl groups. Some exemplary high-density hydroxyl groups-containing dendrimers include commercially available polyester dendritic polymer such as hyperbranched 2,2-Bis(hydroxyl-methyl)propionic acid polyester polymer (for example, hyperbranched bis-MPA polyester-64-hydroxyl, generation 4), dendritic polyglycerols.

In some embodiments, the high-density hydroxyl groups-containing dendrimers are oligo ethylene glycol (OEG)-like dendrimers. For example, a generation 2 OEG dendrimer (D2-OH-60) can be synthesized using highly efficient, robust and atom economical chemical reactions such as Cu (I) catalyzed alkyne-azide click and photo catalyzed thiol-ene click chemistry. Highly dense polyol dendrimer at very low generation in minimum reaction steps can be achieved by using an orthogonal hypermonomer and hypercore strategy, for example as described in International Patent Publication No. WO2019094952. In some embodiments, the dendrimer backbone has non-cleavable polyether bonds throughout the structure to avoid the disintegration of dendrimer in vivo and to allow the elimination of such dendrimers as a single entity from the body (non-biodegradable).

In some embodiments, the dendrimer is able to specifically target a particular tissue region and/or cell type, pro-inflammatory macrophages involved in ALI/ARDS. In preferred embodiments, the dendrimer is able to specifically target a particular tissue region and/or cell type without a targeting moiety.

In preferred embodiments, the dendrimers have a plurality of hydroxyl (—OH) groups on the periphery of the dendrimers. The preferred surface density of hydroxyl (—OH) groups is at least 1 OH group/nm$^2$ (number of hydroxyl surface groups/surface area in nm$^2$). For example, in some embodiments, the surface density of hydroxyl groups is more than 2, 3, 4, 5, 6, 7, 8, 9, 10; preferably at least 10, 15, 20, 25, 30, 35, 40, 45, 50, or more than 50. In further embodiments, the surface density of hydroxyl (—OH) groups is between about 1 and about 50, preferably 5-20 OH group/nm$^2$ (number of hydroxyl surface groups/surface area in nm$^2$) while having a molecular weight of between about 500 Da and about 10 kDa.

In some embodiments, the dendrimers may have a fraction of the hydroxyl groups exposed on the outer surface, with the others in the interior core of the dendrimers. In preferred embodiments, the dendrimers have a volumetric density of hydroxyl (—OH) groups of at least 1 OH group/nm$^3$ (number of hydroxyl groups/volume in nm$^3$). For example, in some embodiments, the volumetric density of hydroxyl groups is 2, 3, 4, 5, 6, 7, 8, 9, 10, or more than 10, 15, 20, 25, 30, 35, 40, 45, and 50. In some embodiments, the volumetric density of hydroxyl groups is between about 4 and about 50 groups/nm$^3$, preferably between about 5 and about 30 groups/nm$^3$, more preferably between about 10 and about 20 groups/nm$^3$.

B. Coupling Agents and Spacers

Dendrimer complexes can be formed of therapeutically active agents or compounds conjugated or attached to a dendrimer, a dendritic polymer or a hyperbranched polymer. Optionally, the active agents are conjugated to the dendrimers via one or more spacers/linkers via different linkages such as disulfide, ester, carbonate, carbamate, thioester, hydrazine, hydrazides, and amide linkages. The one or more spacers/linkers between a dendrimer and an agent can be designed to provide a releasable or non-releasable form of the dendrimer-active complexes in vivo. In some embodiments, the attachment occurs via an appropriate spacer that provides an ester bond between the agent and the dendrimer. In some embodiments, the attachment occurs via an appropriate spacer that provides an amide bond between the agent and the dendrimer. In preferred embodiments, one or more spacers/linkers between a dendrimer and an agent are added to achieve desired and effective release kinetics in vivo.

The term "spacers" as used herein includes compositions used for linking a therapeutically active agent to the dendrimer. The spacer can be either a single chemical entity or two or more chemical entities linked together to bridge the polymer and the therapeutic agent or imaging agent. The spacers can include any small chemical entity, peptide or polymers having sulfhydryl, thiopyridine, succinimidyl, maleimide, vinylsulfone, and carbonate terminations.

The spacer can be chosen from among a class of compounds terminating in sulfhydryl, thiopyridine, succinimidyl, maleimide, vinylsulfone and carbonate group. The spacer can include thiopyridine terminated compounds such as dithiodipyridine, N-Succinimidyl 3-(2-pyridyldithio)-propionate (SPDP), Succinimidyl 6-(3-[2-pyridyldithio]-propionamido)hexanoate LC-SPDP or Sulfo-LC-SPDP. The spacer can also include peptides wherein the peptides are linear or cyclic essentially having sulfhydryl groups such as glutathione, homocysteine, cysteine and its derivatives, arg-gly-asp-cys (RGDC), cyclo(Arg-Gly-Asp-d-Phe-Cys) (c(RGDfC)), cyclo(Arg-Gly-Asp-D-Tyr-Cys), cyclo(Arg-Ala-Asp-d-Tyr-Cys). The spacer can be a mercapto acid derivative such as 3 mercapto propionic acid, mercapto acetic acid, 4 mercapto butyric acid, thiolan-2-one, 6 mercaptohexanoic acid, 5 mercapto valeric acid and other mercapto derivatives such as 2 mercaptoethanol and 2 mercaptoethylamine. The spacer can be thiosalicylic acid and its derivatives, (4-succinimidyloxycarbonyl-methyl-alpha-2-pyridylthio)toluene, (3-[2-pyridithio]propionyl hydrazide, The spacer can have maleimide terminations wherein the spacer includes polymer or small chemical entity such as bis-maleimido diethylene glycol and bis-maleimido triethylene glycol, Bis-Maleimidoethane, bismaleimidohexane. The spacer can include vinylsulfone such as 1,6-Hexane-bis-vinylsulfone. The spacer can include thioglycosides such as thioglucose. The spacer can be reduced proteins such as bovine serum albumin and human serum albumin, any thiol terminated compound capable of forming disulfide bonds The spacer can include polyethylene glycol having maleimide, succinimidyl and thiol terminations.

The agent and/or targeting moiety can be either covalently attached or intra-molecularly dispersed or encapsulated. The dendrimer is preferably a PAMAM dendrimer up to generation 10, having carboxylic, hydroxyl, or amine terminations. In preferred embodiments, the dendrimer is linked to agents via a spacer ending in disulfide, ester or amide bonds.

C. Therapeutic, Prophylactic, and Diagnostic Active Agents

Agents to be included in the particles to be delivered can be proteins or peptides, sugars or carbohydrate, nucleic acids or oligonucleotides, lipids, small molecules (e.g., molecular weight less than 2000 Dalton, preferably less than 1500 Dalton, more preferably 300-700 Dalton), or combinations thereof. The nucleic acid can be an oligonucleotide encoding a protein, for example, a DNA expression cassette or an mRNA. Representative oligonucleotides include siRNAs, microRNAs, DNA, and RNA. In some embodiments, the active agent is a therapeutic antibody.

Dendrimers have the advantage that multiple therapeutic, prophylactic, and/or diagnostic agents can be delivered with the same dendrimers. One or more types of active agents can be encapsulated, complexed or conjugated to the dendrimer. In one embodiment, the dendrimers are complexed with or conjugated to two or more different classes of agents, providing simultaneous delivery with different or independent release kinetics at the target site. In another embodiment, the dendrimers are covalently linked to at least one detectable moiety and at least one class of agents. In a further embodiment, dendrimer complexes each carrying different classes of agents are administered simultaneously for a combination treatment. Exemplary active agents include therapeutic agents useful for treating and preventing SARS and ARDS.

1. Anti-Inflammatory Agents

In some embodiments, the compositions include one or more anti-inflammatory agents. Anti-inflammatory agents reduce inflammation and include steroidal and non-steroidal drugs.

Preferred NSAIDS include mefenamic acid, aspirin, Diflunisal, Salsalate, Ibuprofen, Naproxen, Fenoprofen, Ketoprofen, Deacketoprofen, Flurbiprofen, Oxaprozin, Loxoprofen, Indomethacin, Sulindac, Etodolac, Ketorolac, Diclofenac, Nabumetone, Piroxicam, Meloxicam, Tenoxicam, Droxicam, Lornoxicam, Isoxicam, Meclofenamic acid, Flufenamic acid, Tolfenamic acid, elecoxib, Rofecoxib, Valdecoxib, Parecoxib, Lumiracoxib, Etoricoxib, Firocoxib, Sulphonanilides, Nimesulide, Niflumic acid, and Licofelone.

A preferred anti-inflammatory is an antioxidant drug including N-acetylcysteine. Structure of N-acetylcysteine is shown as Structure II below.

Structure II

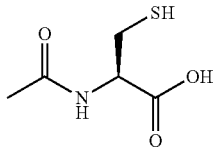

Representative small molecules include steroids such as methyl prednisone, dexamethasone, non-steroidal anti-inflammatory agents including COX-2 inhibitors, corticosteroid anti-inflammatory agents, gold compound anti-inflammatory agents, immunosuppressive, anti-inflammatory and anti-angiogenic agents, anti-excitotoxic agents such as valproic acid, D-aminophosphonovalerate, D-aminophosphonoheptanoate, inhibitors of glutamate formation/release, such as baclofen, NMDA receptor antagonists, salicylate anti-inflammatory agents, ranibizumab, anti-VEGF agents, including aflibercept, and rapamycin. Other anti-inflammatory drugs include nonsteroidal drug such as indomethacin, aspirin, acetaminophen, diclofenac sodium and ibuprofen. The corticosteroids can be fluocinolone acetonide and methylprednisolone.

Exemplary immune-modulating drugs include cyclosporine, tacrolimus and rapamycin. In some embodiments, anti-inflammatory agents are biologic drugs that block the action of one or more immune cell types such as T cells, or block proteins in the immune system, such as tumor necrosis factor-alpha (TNF-alpha), interleukin 17-A, interleukin-12, and interleukin-23.

In some embodiments, the anti-inflammatory drug is a synthetic or natural anti-inflammatory protein. Antibodies specific to select immune components can be added to immunosuppressive therapy. In some embodiments, the anti-inflammatory drug is an anti-T cell antibody (e.g., anti-thymocyte globulin or Anti-lymphocyte globulin), anti-IL-2Rα receptor antibody (e.g., basiliximab or daclizumab), or anti-CD20 antibody (e.g., rituximab).

Inflammatory diseases may be linked to pathologically elevated signaling via the receptor for lipopolysaccharide (LPS), toll-like receptor 4 (TLR4). For example, one study showed that ventilator-induced inflammatory lung injury (VILI) is mechanistically linked to increased NAMPT transcription and circulating levels of nicotinamide phosphoribosyl-transferase (NAMPT/PBEF), which induces lung NFκB transcriptional activities and inflammatory injury via direct ligation of TLR4. There has been great interest in the discovery of TLR4 inhibitors as potential anti-inflammatory agents. Recently, the structure of TLR4 bound to the inhibitor E5564 was solved, enabling design and synthesis of new TLR4 inhibitors that target the E5564-binding domain. These are described in U.S. Pat. No. 8,889,101. As reported by Neal, et al., PLoS One. 2013; 8(6): e65779e, a similarity search algorithm used in conjunction with a limited screening approach of small molecule libraries identified compounds that bind to the E5564 site and inhibit TLR4. The lead compound, C34, is a 2-acetamidopyranoside (MW 389) with the formula $C_{17}H_{27}NO_9$, which inhibits TLR4 in enterocytes and macrophages in vitro, and reduces systemic inflammation in mouse models of endotoxemia and necrotizing enterocolitis. Thus, in some embodiments, the active agents are one or more TLR4 inhibitors. In preferred embodiments, the active agents are C34, and derivatives, analogues thereof.

In preferred embodiments, the one or more anti-inflammatory drugs are released from the dendrimer complexes after administration to a mammalian subject in an amount effective to inhibit inflammation for at least 1 day, 2 days, 3 days, 4 days, 5 days, 6 days, preferably at least a week, 2 weeks, or 3 weeks, more preferably at least a month, two months, three months, four months, five months, or six months.

2. Additional Active Agents to be Delivered

In some embodiments, the dendrimers are used to deliver one or more additional active agents, particularly one or more active agents to prevent or treat one or more symptoms of infectious diseases. Suitable therapeutic, diagnostic, and/or prophylactic agents can be a biomolecule, such as an enzyme, protein, polypeptide, or nucleic acid or a small molecule agent (e.g., molecular weight less than 2000 Dalton, preferably less than 1500 Dalton), including organic, inorganic, and organometallic agents. The additional agent can be encapsulated within the dendrimers, dispersed within the dendrimers, and/or associated with the surface of the dendrimer, either covalently or non-covalently.

a. Therapeutic and Prophylactic Agents

In the primary embodiment, the dendrimer is complexed to N-acetyl cysteine.

In some embodiments, the dendrimer complexes include one or more therapeutic, prophylactic, or prognostic agents that are complexed or conjugated to the dendrimers. Representative therapeutic agents include, but are not limited to, neuroprotective agents, anti-inflammatory agents, antioxidants, anti-infectious agents, and combinations thereof.

In some embodiments the dendrimers deliver one or more oligonucleotides. Representative oligonucleotides include siRNAs, microRNAs, DNA, and RNA.

In some embodiments, the active agent is an anti-infectious agent. Exemplary anti-infectious agents include anti-viral agents, antibacterial agents, antiparasitic agents, and anti-fungal agents.

In some embodiments, the dendrimers deliver one or more therapeutic agents that have been shown to have efficacy for treating and preventing SARS and or ARDS. In some embodiments, the dendrimers deliver one or more therapeutic agents that have been shown to have efficacy for treating and preventing COVID-19. Exemplary therapeutic agents include anti-viral agents and immunomodulatory agents, including but not-limited to hydroxychloroquine, EIDD-2801, Remdesivir, Lopinavir, and Ritonavir and cytokine inhibitors.

3. Diagnostic Agents

In some cases, the agent may include a diagnostic. Examples of diagnostic agents include paramagnetic molecules, fluorescent compounds, magnetic molecules, and radionuclides, x-ray imaging agents, and contrast media. Examples of other suitable contrast agents include gases or gas emitting compounds, which are radiopaque. Dendrimer complexes can further include agents useful for determining the location of administered compositions. Agents useful for this purpose include fluorescent tags, radionuclides and contrast agents.

Exemplary diagnostic agents include dyes, fluorescent dyes, near infra-red dyes, SPECT imaging agents, PET imaging agents and radioisotopes.

In further embodiments, a singular dendrimer complex composition can simultaneously treat and/or diagnose a disease or a condition at one or more locations in the body.

III. Methods of Use

The dendrimer compositions can be used to treat or prevent one or more symptoms of severe inflammation in an organ of a human in need thereof. The methods of treating or preventing one or more symptoms of severe inflammation include administering to the human dendrimers complexed, covalently conjugated, or intra-molecularly dispersed or encapsulated with one or more therapeutic or prophylactic agents, in an amount effective to treat, alleviate or prevent one or more symptoms of severe inflammation.

In some embodiments, the dendrimer compositions can be used to treat and/or diagnose one or more respiratory disorders and/or diseases. In some embodiments, the dendrimer complexes are used to treat ARDS, for example, those caused by a pathogenic viral infection such as COVID-19. In another embodiment, the dendrimer complexes are used to treat one or more symptoms associated with ventilator-induced lung injury (VILI), including barotrauma, volutrauma, atelectrauma, and biotrauma.

The methods typically include administering to a subject in a need thereof an effective amount of a composition including dendrimer and one or more agents to treat and/or alleviate one or more symptoms associated with the respiratory disorders and/or diseases. In preferred embodiments, the dendrimer compositions including one or more anti-inflammatory agents or formulations thereof are administered in an amount effective reduce inflammation in the respiratory tract.

Methods for reducing vascular leakage or vascular permeability in the respiratory tract are also described. Diseases that present the symptoms of increased vascular leakage or increased vascular permeability in the lung can be characterized generally as vascular permeability disorders in the lung, including ALI, ARDS, and VILI. In some embodiments, the dendrimer compositions reduce and/or alleviate the increased vascular leakage and permeability of these vascular disordered in the lung. Permeability of pulmonary endothelial cells and pulmonary alveolar cells can be assessed by the protein levels and cell count in the bronchoalveolar lavage (BAL) of a mammal, wherein higher protein levels or cell count in the BAL as compared to control indicates increased pulmonary endothelial and epithelial permeability. Accordingly, methods for decreasing BAL protein levels or BAL cell count in a mammal including the step of administering to a mammal in need thereof an effective amount of the dendrimer compositions are also provided.

Methods for treating or ameliorating one or more symptoms of lung disorders or diseases are described. In particular, the compositions are used in an amount effective for treating or ameliorating one or more symptoms of ALI and ARDS, for example, those associated with COVID-19. The clinical features of COVID-19 are varied, ranging from asymptomatic state to acute respiratory distress syndrome and multi organ dysfunction. Thus, in some embodiments, the dendrimer compositions are administered in an amount effective to reduce mortality rate, to reduce occurrence of organ failure, to reduce hospitalization time.

Acute lung injury, particularly ARDS, involves an intense inflammatory response in the lungs, with accumulation of both pro- and anti-inflammatory cytokines in bronchoalveolar lavage fluid (BALF). In some embodiments, the dendrimer compositions are used in an amount effective for decreasing production of pro-inflammatory cytokines, and/or promoting generation of anti-inflammatory cytokines, and/or anti-inflammatory phenotype of one or more immune cell types. In other embodiments, the compositions are used to suppress pro-inflammatory and promote anti-inflammatory properties of one or more immune cells involved in the one or more lung conditions/diseases to be treated.

In some embodiments, the compositions are administered in an amount effective to inhibit or reduce one or more pro-inflammatory cytokines such as C-reactive protein (CRP), ferritin, TNF-α, IL-6, IL-12, IL-1β, and IL-18; to inhibit or reduce one or more chemokines and/or chemokines receptors such as CXCL-8, CXCL-1, CXCL-5, and CCL-2, Monocyte chemoattractant protein-1 (MCP-1); and/or to inhibit or reduce reactive oxygen species. In further embodiments, the compositions can increase production of anti-inflammatory cytokines such as IL-10. In some embodiments, the compositions are administered in an amount effective to inhibit or reduce inducible NO synthase (iNOS) in activated macrophages in the disease/damaged lung.

Pro-inflammatory cells or inflammatory cells refer to immune cells that promote pro-inflammatory activities, secretion of pro-inflammatory cytokines such as IL-12, IFN-γ, and TNF-α, or a combination thereof. Exemplary pro-inflammatory cells including pro-inflammatory M1 macrophages or classically activated macrophages (CAMs). In some embodiments, methods for depleting, inhibiting or reducing pro-inflammatory alveolar macrophages or classically activated macrophages (M1-like macrophages) in a subject, for example, by blocking proliferation, migration, or activation of the pro-inflammatory alveolar macrophages, are described. The methods include administering to the subject the dendrimer complexes including one or more active agents an effective amount to deplete, inhibit, or reduce the number or activities of the pro-inflammatory M1 macrophages by 10%, 20%, 30%, 40%, 50%, 60%, 70%, 80%, 90%, 100%, 150%, 200%, 250%, 300%, or more than 300% relative to such levels before treatment with the dendrimer compositions.

In some embodiments, the compositions and formulations thereof are used for reducing/inhibiting an inflammatory response in a subject in need thereof by administering an effective amount of the compositions to reduce activation, proliferation and/or recruitment of one or more pro-inflammatory cells, and/or enhance activation, proliferation and/or recruitment of one or more suppressive immune cells are provided. In some embodiments, the pro-inflammatory cells are pro-inflammatory M1 macrophages. In further embodiments, the suppressive immune cells are M2-like macrophages. Thus, in some embodiments, the compositions can promote the switch from a pro-inflammatory phenotype (M1 macrophage) to an anti-inflammatory state (M2 macrophage) at one or more diseased tissues/organs including the lung, by reducing proliferation and/or generation of M1 macrophage, to enhance activation, proliferation and/or generation of M2 macrophages, and/or to increase the ratio of M2 macrophages to M1 macrophages, effective to ameliorate one or more symptoms of an inflammatory condition such as ALI and ARDS.

In some embodiments, the compositions and formulations thereof are used for reducing in hospitalization time, mortality, cardiac injury markers, pro-inflammatory cytokine levels, organ failure, days/time with hypoxemia, reducing dependence on supplemental oxygen, reducing dependence on mechanical ventilation, improve blood oxygenation, and/or improving survival rate.

All the methods can include the step of identifying and selecting a subject in need of treatment, or a subject who would benefit from administration with the compositions.

A. Methods for Treating Respiratory Diseases and Disorders

In general, the compositions and methods of treatment thereof can be used for various lung disorders, diseases, or injuries, including, but not limited to, ALI, ARDS, and VILI. The compositions can also be used for treatment of other inflammatory diseases, disorders, and injuries.

The compositions or formulations thereof may be administered to mammalian subjects, including but not limited to humans, primates such as monkeys and apes, canines such as dogs, felines such as cats, bovines such as cows, equines such as horses, swine such as pigs, and rodents such as mice and rats. In preferred embodiments, the subject to be treated is a human.

In preferred embodiments, the dendrimers are used to treat or prevent Acute Lung Injury (ALI) and/or Acute Respiratory Distress Syndrome (ARDS).

Acute lung injury (ALI) and acute respiratory distress syndrome (ARDS) are life-threatening diseases in critically ill patients. They are the manifestations of an inflammatory response of the lung to both direct and indirect insults and are characterized by severe hypoxemia, hypercapnia, diffuse infiltration in the chest X-ray, and a substantial reduction in pulmonary compliance.

The term "acute lung injury" or "ALI," as opposed to chronic lung injury or condition, refers to a diffuse heterogeneous lung injury characterized by hypoxemia, non-cardiogenic pulmonary edema, low lung compliance, alveolar cell permeability, and widespread capillary leakage. The appearance of the symptoms of acute lung injury can vary depending on the cause of the injury—it takes hours or days in endotoxin-induced injury, while it can take weeks in radiation induced lung injury. ALI can be caused by stimulus of local or systemic inflammation, ionizing irradiation, infection, and exposure to bacterial endotoxin, sepsis, or trauma in the lung. Clinically, ALI can be diagnosed using one or more of the following parameters: bilateral pulmonary infiltrates on chest radiograph consistent with the presence of edema and no clinical evidence of left atrial hypertension; pulmonary capillary wedge pressure <18 mmHg (2.4 kPa); and $PaO_2/FiO_2$<300 mmHg (40 kPa), where $PaO_2$ is the partial pressure of oxygen and $FiO_2$ is the fraction of inspired oxygen. The core pathology of ALI is disruption of the capillary-endothelial barrier, decreased endothelial integrity and increased pulmonary alveolar permeability. Disruption of endothelial barrier can result in protein-rich fluid leaking out of the capillaries. Acute lung injury can lead to chronic lung conditions, which is generally characterized by lung tissue remodeling and fibrosis.

ARDS, the most severe form of ALI, is defined by a ratio of arterial oxygen to fraction of inspired oxygen of about 200 mmHg or less, regardless of the level of positive end-expiratory pressure (PEEP). Although the term ARDS is often used interchangeably with ALI, by strict criteria, ARDS should be reserved for the most severe form of the disease (Bernard GR et al., Am J Respir Crit Care Med. 1994; 149:818-24; Artigas A et al., Intensive Care Med. 1998; 24:378-98). The methods using dendrimers conjugated or complexed with one or more anti-inflammatory agents are suitable for treating a subject with ARDS with varying degree of severity including mild ($PaO_2/FiO_2$ between 200 and 300 mmHg), moderate ($PaO_2/FiO_2$ between 100 and 200 mmHg), and severe ($PaO_2/FiO_2$<100 mmHg). The methods include administering to a subject in need thereof an effective amount of the dendrimer composition to improve oxygenation, i.e., to improve $PaO_2/FiO_2$. In preferred embodiments, the compositions or formulations thereof are administered to a subject with ARDS caused by highly pathogenic coronavirus such as SARS-CoV-2 in an amount effective to treat and/or alleviate one or more symptoms of ARDS.

In some embodiments, pulse oximetry-based peripheral blood oxygen saturation (SpO2)/$FiO_2$ ($SpO_2/FiO_2$) ratios are used to monitor patients with ARDS. $SpO_2/FiO_2$ ratios are ubiquitously available and noninvasive. Studies suggest that $SpO_2/FiO_2$ and $PaO_2/FiO_2$ ratios are reasonably well correlated, particularly when $PaO_2/FiO_2$ ratios are less than 300, a patient had severe hypoxemia, defined by an $SpO_2/FiO_2$ ratio less than 150 (corresponding to a $PaO_2/FiO_2$≤100). The methods using dendrimers conjugated or complexed with one or more anti-inflammatory agents are suitable for treating a subject with ARDS with varying degree of severity including mild ($SpO_2/FiO_2$ ratio 235-314), moderate ($SpO_2/FiO_2$ ratio 150-234), and severe ($SpO_2/FiO_2$ ratio <150). The methods include administering to a subject in need thereof an effective amount of the dendrimer composition to improve oxygenation, i.e., to improve $SpO_2/FiO_2$ ratios. In preferred embodiments, methods include administering to a subject in need thereof an effective amount of the dendrimer composition to reduce dependence of supplemental oxygen usage and/or mechanical ventilation.

ALI can be caused by a variety of means, such as ionizing radiation. "Radiation-induced lung injury" or "RILI" is a general term for injuries sustained by the lungs as a result of exposure to ionizing radiation, which most commonly occurs as a result of radiation therapy of thoracic cancer. Such damage includes early (acute) inflammatory damage (radiation pneumonitis) and later complications of chronic scarring (radiation fibrosis). RILI is a particular subset of ALI, with a unique patient population (most commonly patients receiving radiation therapy), unique nature of injury (radiation-induced injury), and a slight delay of onset of disease (weeks vs. hours/days as compared with LPS-induced ALI). Clinically, RILI may be characterized by loss of epithelial cells, edema, inflammation, and occlusions of airways, air sacs, and blood vessels. The lungs are the most radiosensitive organ, and radiation pneumonitis can lead to pulmonary insufficiency and death (100% after exposure to 50 Gy of radiation) in a few months. Injuries most suitable for treatment of the instant application include inflammatory damage (radiation pneumonitis) manifested by increased pulmonary permeability.

ALI can also be induced by bacterial endotoxin. The term "endotoxin" refers to a toxin produced by Gram-negative or Gram-positive bacteria. More specifically, an endotoxin is a structural molecule of a bacterium that is recognized by the immune system. Prototypical examples of endotoxin are lipopolysaccharide (LPS) or lipooligosaccharide (LOS) found in the outer membrane of various Gram-negative bacteria, including *Escherichia coli*, and are an important component of their ability to cause disease. LPS includes of a polysaccharide (sugar) chain and a lipid moiety, known as lipid A, which is responsible for the toxic effects. The polysaccharide chain is highly variable amongst different bacteria. Endotoxins are in large part responsible for the dramatic clinical manifestations of infections with pathogenic Gram-negative bacteria, such as *Neisseria meningitidis*, the pathogens that causes meningococcal disease, including meningococcemia, Waterhouse-Friderichsen syndrome and meningitis. Other endotoxins include the delta endotoxin of *Bacillus thuringiensis*, which makes crystal-like inclusion bodies next to the endospore inside the bacteria. In addition, *Listeria monocytogenes* may produce an "endotoxin-like" substance.

ALI can also be caused by trauma. "Trauma" refers to a body wound, or shock produced by sudden physical injury in the lung, as from violence or accident. The effects of disruption of the endothelial barrier as a result of physical injury can be alleviated by the methods.

As part of the therapy for the underlying disease (such as shock, trauma, sepsis, pneumonia, aspiration, or burns), mechanical ventilation is critical for resolving life-threatening hypoxia and hypercapnia. However, studies from experimental and clinical fields have shown that mechanical ventilation, if performed incautiously, will further damage the lungs due to overinflation, barotrauma, and cyclic closing and reopening of the alveoli. This phenomenon has been named ventilator-associated lung injury (VALI). Furthermore, the mechanism of VALI can cause or trigger a pulmonary and systemic inflammatory reaction that may further lead to multiple organ dysfunction and multiple system organ failure. The methods using dendrimers conjugated or complexed with one or more anti-inflammatory agents are suitable for treating a patient with VALI. In preferred embodiments, the compositions or formulations thereof are administered to a subject with VALI in an amount effective to treat and/or alleviated one or more symptoms of VALI.

The pathogenesis of ALI and ARDS on different levels (cellular, molecular, and so on) are well established (Ashbaugh, et al., Lancet. 1967; 2:319-23; Ware, et al., N Engl J Med. 2000; 342:1334-49; Rocco, et al., Zin. Curr Opin Crit Care. 2005; 11:10-7; 14. Ricard et al., Curr Opin Crit Care. 2002; 8:12-20). In brief, the alveolar-capillary unit is composed of the alveolar endothelium and the microvascular endothelium. Whatever insult is applied to the lung, it will result in more or less diffuse damage to this blood-gas barrier and, therefore, impair gas exchange. In pulmonary ARDS, the insult hits the alveolar endothelium primarily (e.g., pneumonia, aspiration), whereas in extrapulmonary ARDS (e.g., sepsis, pancreatitis, shock) the microvascular endothelium is the target. However, at a distinct point in the disease both entities react relatively uniformly with a diffuse inflammation of lung tissue. The host's redundant inflammatory network is the key factor in the development and progression of ARDS. Starting either from the alveolar or the microvascular side, the inflammatory process leads to alveolar and interstitial edema, reduced alveolar fluid clearance, impairment of surfactant production and function, and lung fibrosis. The persistent elevation of inflammatory mediators (mostly of neutrophil origin) in the bronchoalveolar-lavage precludes a resolution of the inflammatory process in the lungs. Due to gravity, in the supine position formation of edema is pronounced in dorsal basal areas, which leads to atelectasis, cyclic closing and reopening of alveoli, and loss of gas exchange lung surface. Moreover, this results in pronounced ventilation/perfusion mismatching, intrapulmonary shunting, pulmonary hypertension, reduced lung compliance, and global respiratory failure. The release of inflammatory mediators from damaged lung tissue triggers systemic inflammation (SIRS) and may lead to multiple organ failure, which is the main cause of death in ARDS patients.

Accordingly, the dendrimer compositions or formulations thereof are administered to a mammalian subject, preferably human, in an amount effective to reduce vascular leakage or vascular permeability in the lung, to increase alveolar cell integrity or endothelial cell integrity in the lung, and/or reduce bronchoalveolar lavage (BAL) protein levels or BAL cell count.

1. Dosage and Effective Amounts

Dosage and dosing regimens are dependent on the severity and location of the disorder or injury and/or methods of administration, and is known to those skilled in the art. A therapeutically effective amount of the dendrimer composition used in the treatment of lung disorders and/or diseases is typically sufficient to reduce or alleviate one or more symptoms of lung disorders and/or diseases.

Preferably the active agents do not target or otherwise modulate the activity or quantity of healthy cells not within or associated with the diseased/damaged lung or do so at a reduced level compared to cells associated with the diseased/damaged lung. In this way, by-products and other side effects associated with the compositions are reduced.

A pharmaceutical composition including a therapeutically effective amount of the dendrimer compositions and a pharmaceutically acceptable diluent, carrier or excipient is described. In some embodiments, the pharmaceutical compositions include an effective amount of hydroxyl-terminated PAMAM dendrimers conjugated to N-acetyl cysteine. In some particular embodiments, dosage ranges suitable for use are between about 0.1 mg/kg body weight of the recipient and about 100 mg/kg body weight of the recipient, inclusive; between about 0.5 mg/kg and about 40 mg/kg, inclusive; between about 1.0 mg/kg and about 20 mg/kg, inclusive; and between about 2.0 mg/kg and about 10 mg/kg, inclusive. In some embodiments, the composition is administered in a dosage of between about 20 mg/kg body weight of the recipient and about 40 mg/kg body weight of the recipient, inclusive. For example, in some embodiments, a composition including dendrimer/N-acetylcysteine (D-NAC) is administered intravenously in a dosage of between about 20 mg/kg body weight of the recipient and about 40 mg/kg body weight of the recipient, inclusive. In other embodiments, the composition is administered in a dosage of between about 2 mg/kg body weight of the recipient and about 8 mg/kg body weight of the recipient, inclusive. For example, in some embodiments, a composition including dendrimer/N-acetylcysteine (D-NAC) is administered subcutaneously in a dosage of between about 2 mg/kg body weight of the recipient and about 8 mg/kg body weight of the recipient, inclusive.

Dosage forms of the pharmaceutical composition including the dendrimer compositions are also provided. "Dosage form" refers to the physical form of a dose of a therapeutic compound, such as a capsule or vial, intended to be administered to a patient. The term "dosage unit" as used herein refers to the amount of the therapeutic compounds to be administered to a patient in a single dose. In some embodiments, the dosage unit suitable for use are (assuming the weight of an average patient being 70 kg) between 5 mg/dosage unit and about 7000 mg/dosage unit, inclusive; between about 35 mg/dosage unit and about 2800 mg/dosage unit, inclusive; and between about 70 mg/dosage unit and about 1400 mg/dosage unit, inclusive; between about 150 mg/dosage unit and about 700 mg/dosage unit, inclusive; and between about 400 mg/dosage unit and about 600 mg/dosage unit, inclusive.

The actual effective amounts of dendrimer complex can vary according to factors including the specific active agent administered, the particular composition formulated, the mode of administration, and the age, weight, condition of the subject being treated, as well as the route of administration and the disease or disorder. The subjects are preferably humans. Generally, for intravenous injection or infusion, the dosage may be lower than for topical, local or regional administration.

In general, the timing and frequency of administration will be adjusted to balance the efficacy of a given treatment or diagnostic schedule with the side-effects of the given delivery system. Exemplary dosing frequencies include continuous infusion, single and multiple administrations such as hourly, daily, weekly, monthly, or yearly dosing.

In some embodiments, doses are administered once, twice, or three times daily, or every other day, two days, three days, four days, five days, or six days to a human. In some embodiments, doses are administered about once or twice every week, every two weeks, every three weeks, or every four weeks. In some embodiments, doses are administered about once or twice every month, every two months, every three months, every four months, every five months, or every six months.

It will be understood by those of ordinary skill that a dosing regimen can be any length of time sufficient to treat the disorder in the subject. In some embodiments, the regimen includes one or more cycles of a round of therapy followed by a drug holiday (e.g., no drug). The drug holiday can be 1, 2, 3, 4, 5, 6, or 7 days; or 1, 2, 3, 4 weeks, or 1, 2, 3, 4, 5, or 6 months.

2. Controls

The effect of the dendrimer compositions including one or more agents can be compared to a control. Suitable controls are known in the art and include, for example, an untreated subject, or a placebo-treated subject. A typical control is a comparison of a condition or symptom of a subject prior to and after administration of the targeted agent. The condition or symptom can be a biochemical, molecular, physiological, or pathological readout. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or average determined based on measuring the symptom, pharmacologic, or physiologic indicator in one or more subjects that do not have the disease or condition to be treated (e.g., healthy subjects). In some embodiments, the effect of the treatment is compared to a conventional treatment that is known the art.

B. Combination Therapies and Procedures

The compositions can be administered alone or in combination with one or more conventional therapies. In some embodiments, the conventional therapy includes administration of one or more of the compositions in combination with one or more additional active agents. The combination therapies can include administration of the active agents together in the same admixture, or in separate admixtures. Therefore, in some embodiments, the pharmaceutical composition includes two, three, or more active agents. Such formulations typically include an effective amount of an agent targeting the site of treatment. The additional active agent(s) can have the same or different mechanisms of action. In some embodiments, the combination results in an additive effect on the treatment of the lung condition. In some embodiments, the combinations result in a more than additive effect on the treatment of the disease or disorder.

The additional therapy or procedure can be simultaneous or sequential with the administration of the dendrimer composition. In some embodiments, the additional therapy is performed between drug cycles or during a drug holiday that is part of the dosage regime. For example, in some embodiments, the additional therapy or procedure is damage control surgery, fluid resuscitation, blood transfusion, bronchoscopy, and/or drainage.

In further embodiments, the additional therapy or procedure is prone positioning, recruitment maneuver, inhalation of NO, extracorporeal membrane oxygenation (ECMO), intubation, and/or inhalation of $PGI_2$. A prone position enhances lung recruitment in a potentially recruitable lung by various mechanisms, releasing the diaphragm, decreasing the effect of heart and lung weight and shape on lung tissue, decreasing the lung compression by the abdomen, and releasing the lower lobes, which improves gas exchange and decreases mortality in severe ARDS patients. ECMO provides extracorporeal gas exchange with no effect on lung recruitment. It affords lung rest and works well for the non-recruitable lung. It has been shown to improve survival for certain groups of patients in high-performance ECMO centers. Additional therapeutic agents can also include one or more of antibiotics, surfactant, corticosteroids, and glucocorticoids.

In some embodiments, the compositions and methods are used prior to or in conjunction, subsequent to, or in alternation with treatment with one or more additional therapies or procedures.

IV. Pharmaceutical Formulations

Pharmaceutical compositions including dendrimers and one or more anti-inflammatory agents such as N-acetyl cysteine may be formulated in a conventional manner using one or more physiologically acceptable carriers including excipients and auxiliaries which facilitate processing of the active compounds into preparations which can be used pharmaceutically. Proper formulation is dependent upon the route of administration chosen. In preferred embodiments, the compositions are formulated for parenteral delivery. In some embodiments, the compositions are formulated for subcutaneous injection. Typically, the compositions are formulated in sterile saline or buffered solution for injection into the tissues or cells to be treated. The compositions can be stored lyophilized in single use vials for rehydration immediately before use. Other means for rehydration and administration are known to those skilled in the art.

In some embodiments, the compositions including a generation-4 hydroxyl terminated poly(amidoamine) (PAMAM) dendrimer linked to NAC using a disulfide bond is lyophilized. In a particular embodiment, the composition is lyophilized in a histidine buffer and trehalose. Typically, lyophilized drug product is stable for 12 months at 2-8° C. and for one month at 25° C. In some embodiments, a single dose includes between about 150 mg and about 700 mg, inclusive; between about 400 mg and about 600 mg, inclusive, or between about 450 mg and about 550 mg, inclusive. When reconstituted with sterile water for injection, the resulting solution typically contains 400 mg/mL dendrimer compositions in 20 mM histidine, pH 5.5 with 80 mg/mL trehalose. The dendrimer compositions liquid drug product is formulated at 200 mg/mL in normal saline (9% sodium chloride) at pH 5.5. OP-101 is dosed in human subjects using a mass of dendrimer compositions per kilogram of body weight (mg/kg).

Pharmaceutical formulations contain one or more dendrimer complexes in combination with one or more pharmaceutically acceptable excipients. Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions. See, for example, Remington's Pharmaceutical Sciences, 20th ed., Lippincott Williams & Wilkins, Baltimore, MD, 2000, p. 704.

The compositions are preferably formulated in dosage unit form for ease of administration and uniformity of dosage. The phrase "dosage unit form" refers to a physically discrete unit of conjugate appropriate for the patient to be treated. It will be understood, however, that the total single administration of the compositions will be decided by the attending physician within the scope of sound medical judgment. The therapeutically effective dose can be estimated initially either in cell culture assays or in animal models, usually mice, rabbits, dogs, or pigs. The animal model is also used to achieve a desirable concentration range and route of administration. Such information should then be useful to determine useful doses and routes for administration in humans. Therapeutic efficacy and toxicity of conjugates can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index and it can be expressed as the ratio, LD50/ED50. Pharmaceutical compositions which exhibit large therapeutic indices are preferred. The data obtained from cell culture assays and animal studies can be used in formulating a range of dosages for human use.

Pharmaceutical compositions formulated for administration by parenteral (intramuscular, intraperitoneal, intravenous or subcutaneous injection) and enteral routes of administration are described.

A. Parenteral Administration

The phrases "parenteral administration" and "administered parenterally" are art-recognized terms, and include modes of administration other than enteral and topical administration, such as injections, and include intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intraarticular, subcapsular, subarachnoid, intraspinal and intrastemal injection and infusion. The dendrimers can be administered parenterally, for example, by subdural, intravenous, intrathecal, intraventricular, intraarterial, intra-amniotic, intraperitoneal, or subcutaneous routes. In preferred embodiments, the dendrimer compositions are administered via subcutaneous injection.

For liquid formulations, pharmaceutically acceptable carriers may be, for example, aqueous or non-aqueous solutions, suspensions, emulsions or oils. Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media. The dendrimers can also be administered in an emulsion, for example, water in oil. Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Formulations suitable for parenteral administration can include antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Intravenous vehicles can include fluid and nutrient replenishers, electrolyte replenishers such as those based on Ringer's dextrose. In general, water, saline, aqueous dextrose and related sugar solutions, and glycols such as propylene glycols or polyethylene glycol are preferred liquid carriers, particularly for injectable solutions.

Injectable pharmaceutical carriers for injectable compositions are well-known to those of ordinary skill in the art (see, e.g., Pharmaceutics and Pharmacy Practice, J.B. Lippincott Company, Philadelphia, PA, Banker and Chalmers, eds., pages 238-250 (1982), and ASHP Handbook on Injectable Drugs, Trissel, 15th ed., pages 622-630 (2009)).

In an exemplary embodiment, the composition for administration includes a solution containing 200 mg/mL OP-101 in 10 mM histidine, pH 5.5, with 4.4% trehalose dihydrate. In a particular embodiment the composition is lyophilized. In other embodiments, the composition is in volume between about 0.1 and about 100 ml, inclusive, preferably in a volume of 2.5 mL.

B. Enteral Administration

The compositions can be administered enterally. The carriers or diluents may be solid carriers such as capsule or tablets or diluents for solid formulations, liquid carriers or diluents for liquid formulations, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Vehicles include, for example, sodium chloride solution, Ringer's dextrose, dextrose and sodium chloride, lactated Ringer's and fixed oils. Formulations include, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Vehicles can include, for example, fluid and nutrient replenishers, electrolyte replenishers such as those based on Ringer's dextrose. In general, water, saline, aqueous dextrose and related sugar solutions are preferred liquid carriers. These can also be formulated with proteins, fats, saccharides and other components of infant formulas.

In preferred embodiments, the compositions are formulated for oral administration. Oral formulations may be in the form of chewing gum, gel strips, tablets, capsules or lozenges. Encapsulating substances for the preparation of enteric-coated oral formulations include cellulose acetate phthalate, polyvinyl acetate phthalate, hydroxypropyl methylcellulose phthalate and methacrylic acid ester copolymers. Solid oral formulations such as capsules or tablets are preferred. Elixirs and syrups also are well known oral formulations.

V. Methods of Making Dendrimers and Conjugates or Complexes Thereof

A. Methods of Making Dendrimers

Dendrimers can be prepared via a variety of chemical reaction steps. Dendrimers are usually synthesized according to methods allowing controlling their structure at every stage of construction. The dendritic structures are mostly synthesized by two main different approaches: divergent or convergent.

In some embodiments, dendrimers are prepared using divergent methods, in which the dendrimer is assembled from a multifunctional core, which is extended outward by a series of reactions, commonly a Michael reaction. The strategy involves the coupling of monomeric molecules that possesses reactive and protective groups with the multifunctional core moiety which leads to stepwise addition of generations around the core followed by removal of protecting groups. For example, PAMAM-$NH_2$ dendrimers are first synthesized by coupling N-(2-aminoethyl) acryl amide monomers to an ammonia core.

In other embodiments, dendrimers are prepared using convergent methods, in which dendrimers are built from small molecules that end up at the surface of the sphere, and reactions proceed inward building inward and are eventually attached to a core.

Many other synthetic pathways exist for the preparation of dendrimers, such as the orthogonal approach, accelerated approaches, the Double-stage convergent method or the hypercore approach, the hypermonomer method or the branched monomer approach, the Double exponential method; the Orthogonal coupling method or the two-step approach, the two monomers approach, $AB_2$-$CD_2$ approach.

In some embodiments, the core of the dendrimer, one or more branching units, one or more linkers/spacers, and/or one or more surface groups can be modified to allow conjugation to further functional groups (branching units, linkers/spacers, surface groups, etc.), monomers, and/or active agents via click chemistry, employing one or more Copper-Assisted Azide-Alkyne Cycloaddition (CuAAC), Diels-Alder reaction, thiol-ene and thiol-yne reactions, and azide-alkyne reactions (Arseneault M et al., Molecules. 2015 May 20; 20(5):9263-94). In some embodiments, pre-made dendrons are clicked onto high-density hydroxyl polymers. 'Click chemistry' involves, for example, the coupling of two different moieties (e.g., a core group and a branching unit; or a branching unit and a surface group) via a 1,3-dipolar cycloaddition reaction between an alkyne moiety (or equivalent thereof) on the surface of the first moiety and an azide moiety (e.g., present on a triazine composition or equivalent thereof), or any active end group such as, for example, a primary amine end group, a hydroxyl end group, a carboxylic acid end group, a thiol end group, etc.) on the second moiety.

In some embodiments, dendrimer synthesis replies upon one or more reactions such as thiol-ene click reactions, thiol-yne click reactions, CuAAC, Diels-Alder click reactions, azide-alkyne click reactions, Michael Addition, epoxy opening, esterification, silane chemistry, and a combination thereof.

Any existing dendritic platforms can be used to make dendrimers of desired functionalities, i.e., with a high-density of surface hydroxyl groups by conjugating high-hydroxyl containing moieties such as 1-thio-glycerol or pentaerythritol. Exemplary dendritic platforms such as polyamidoamine (PAMAM), poly (propylene imine) (PPI), poly-L-lysine, melamine, poly (etherhydroxylamine) (PEHAM), poly (esteramine) (PEA) and polyglycerol can be synthesized and explored.

Dendrimers also can be prepared by combining two or more dendrons. Dendrons are wedge-shaped sections of dendrimers with reactive focal point functional groups. Many dendron scaffolds are commercially available. They come in 1, 2, 3, 4, 5, and 6th generations with, respectively, 2, 4, 8, 16, 32, and 64 reactive groups. In certain embodiments, one type of active agents are linked to one type of dendron and a different type of active agent is linked to another type of dendron. The two dendrons are then connected to form a dendrimer. The two dendrons can be linked via click chemistry i.e., a 1,3-dipolar cycloaddition reaction between an azide moiety on one dendron and alkyne moiety on another to form a triazole linker.

Exemplary methods of making dendrimers are described in detail in International Patent Publication Nos. WO2009/046446, WO2015168347, WO2016025745, WO2016025741, WO2019094952, and U.S. Pat. No. 8,889,101.

B. Dendrimer Complexes and Conjugates

Dendrimer complexes can be formed of therapeutic, prophylactic or diagnostic agents conjugated or complexed to a dendrimer, a dendritic polymer or a hyperbranched polymer. Conjugation of one or more agents to a dendrimer are known in the art, and are described in detail in U.S. Published Application Nos. US 2011/0034422, US 2012/0003155, and US 2013/0136697.

In some embodiments, one or more active agents are covalently attached to the dendrimers. In some embodiments, the active agents are attached to the dendrimer via a linking moiety that is designed to be cleaved in vivo. The linking moiety can be designed to be cleaved hydrolytically, enzymatically, or combinations thereof, to provide for the sustained release of the active agents in vivo. Both the composition of the linking moiety and its point of attachment to the active agent, are selected so that cleavage of the linking moiety releases either an active agent, or a suitable prodrug thereof. The composition of the linking moiety can also be selected in view of the desired release rate of the active agents.

In some embodiments, the attachment occurs via one or more of disulfide, ester, ether, thioester, carbamate, carbonate, hydrazine, or amide linkages. In preferred embodiments, the attachment occurs via an appropriate spacer that provides an ester bond or an amide bond between the agent and the dendrimer depending on the desired release kinetics of the active agent. In some cases, an ester bond is introduced for releasable form of active agents. In other cases, an amide bond is introduced for non-releasable form of active agents.

Linking moieties generally include one or more organic functional groups. Examples of suitable organic functional groups include secondary amides (—CONH—), tertiary amides (—CONR—), sulfonamide (—S(O)$_2$—NR—), secondary carbamates (—OCONH—; —NHCOO—), tertiary carbamates (—OCONR—; —NRCOO—), carbonate (—O—C(O)—O—), ureas (—NHCONH—; —NR-CONH—; —NHCONR—, —NRCONR—), carbinols (—CHOH—, —CROH—), disulfide groups, hydrazones, hydrazides, ethers (—O—), and esters (—COO—, —CH$_2$O$_2$C—, CHRO$_2$C—), wherein R is an alkyl group, an aryl group, or a heterocyclic group. In general, the identity of the one or more organic functional groups within the linking moiety can be chosen in view of the desired release rate of the active agents. In addition, the one or more organic functional groups can be chosen to facilitate the covalent attachment of the active agents to the dendrimers. In preferred embodiments, the attachment can occur via an appropriate spacer that provides a disulfide bridge between the agent and the dendrimer. The dendrimer complexes are capable of rapid release of the agent in vivo by thiol exchange reactions, under the reduced conditions found in body.

In certain embodiments, the linking moiety includes one or more of the organic functional groups described above in combination with a spacer group. The spacer group can be composed of any assembly of atoms, including oligomeric and polymeric chains; however, the total number of atoms in the spacer group is preferably between 3 and 200 atoms, more preferably between 3 and 150 atoms, more preferably between 3 and 100 atoms, most preferably between 3 and 50 atoms. Examples of suitable spacer groups include alkyl groups, heteroalkyl groups, alkylaryl groups, oligo- and polyethylene glycol chains, and oligo- and poly(amino acid) chains. Variation of the spacer group provides additional control over the release of the agents in vivo. In embodiments where the linking moiety includes a spacer group, one or more organic functional groups will generally be used to connect the spacer group to both the anti-inflammatory agent and the dendrimers.

Reactions and strategies useful for the covalent attachment of agents to dendrimers are known in the art. See, for example, March, "Advanced Organic Chemistry," 5th Edition, 2001, Wiley-Interscience Publication, New York) and Hermanson, "Bioconjugate Techniques," 1996, Elsevier Academic Press, U.S.A. Appropriate methods for the covalent attachment of a given active agent can be selected in view of the linking moiety desired, as well as the structure of the agents and dendrimers as a whole as it relates to compatibility of functional groups, protecting group strategies, and the presence of labile bonds.

The optimal drug loading will necessarily depend on many factors, including the choice of drug, dendrimer structure and size, and tissues to be treated. In some embodiments, the one or more active drugs are encapsulated, associated, and/or conjugated to the dendrimer at a concentration of about 0.01% to about 45%, preferably about 0.1% to about 30%, about 0.1% to about 20%, about 0.1% to about 10%, about 1% to about 10%, about 1% to about 5%, about 3% to about 20% by weight, and about 3% to about 10% by weight. However, optimal drug loading for any given drug, dendrimer, and site of target can be identified by routine methods, such as those described.

In some embodiments, conjugation of active agents and/or linkers occurs through one or more surface and/or interior groups. Thus, in some embodiments, the conjugation of active agents/linkers occurs via about 1%, 2%, 3%, 4%, or 5% of the total available surface functional groups, preferably hydroxyl groups, of the dendrimers prior to the conjugation. In other embodiments, the conjugation of active agents/linkers occurs on less than 5%, less than 10%, less than 15%, less than 20%, less than 25%, less than 30%, less than 35%, less than 40%, less than 45%, less than 50%, less than 55%, less than 60%, less than 65%, less than 70%, less than 75% total available surface functional groups of the dendrimers prior to the conjugation. In preferred embodiments, dendrimer complexes retain an effective amount of surface functional groups for targeting to specific cell types, whilst conjugated to an effective amount of active agents for treat, prevent, and/or image the disease or disorder.

VI. Kits

The compositions can be packaged in kit. The kit can include a single dose or a plurality of doses of a composition including one or more anti-inflammatory agents encapsulated in, associated with, or conjugated to a dendrimer, and instructions for administering the compositions. Specifically, the instructions direct that an effective amount of the composition be administered to an individual with a particular lung condition/disease such ALI or ARDS as indicated. The composition can be formulated as described above with reference to a particular treatment method and can be packaged in any convenient manner.

The present invention will be further understood by reference to the following non-limiting examples.

EXAMPLES

Example 1: Preparation of Dendrimer-NAC

A PAMAM dendrimer conjugated N-acetylcysteine has been prepared and is in clinical testing. It is referred to as "OP-101". The OP-101 lyophilized drug product includes a solution containing 200 mg/mL OP-101 in 10 mM histidine, pH 5.5, with 4.4% trehalose dihydrate aseptically filled at 2.5 mL per 5 cc vial and lyophilized.

OP-101 includes a poly(amidoamine), or PAMAM, dendrimer which is made of repetitive reactions of methyl acrylate and ethylene diamine. The generation-4, hydroxyl-terminated PAMAM dendrimers, contain an ethylene diamine (EDA) core, amidoamine repeat units ($[CH_2CH_2CONHCH_2CH_2N]$), and 64 hydroxyl end groups (chemical formula: $C_{622}H_{1184}N_{186}O_{188}$). Approximately 20 of the 64 hydroxyls are subsequently converted to amine groups which are then treated with NAC-SPDP to attach N-acetyl cysteine (NAC) units linked via a disulfide bond, as shown in FIG. 1 below. The active component, NAC, is approximately 16% of the total mass of OP-101.

OP-101 has a particle size of approximately 5 nm and a zeta potential of approximately 7 mV. The drug substance is 200 mg/mL OP-101 in an aqueous solution of 0.9% sodium chloride (normal saline) at pH 5.5.

Example 2: Intravenous Administration of OP-101 is Safe in Healthy Volunteers

In this Phase 1 clinical trial study, two cohorts with four subjects dosed per cohort were assessed for adverse events following i.v. administration of large doses of OP-101. Dosages per cohort were as follows: Cohort 1: 20 mg/kg; Cohort 2: 40 mg/kg.

Three subjects had treatment emergent adverse events (Grade 1; urinary casts & proteinuria; one from Cohort 1 and two from Cohort 2). No other treatment emergent adverse events were related to the study drug.

Example 3: Phase 1 Subcutaneous Administration of OP-101 in Healthy Volunteers

In this Phase 1 clinical trial study, two cohorts with four subjects dosed per cohort were assessed for adverse events following subcutaneous (s.c.) administration of large doses of OP-101. Dosages per cohort were as follows: Cohort 1: 4 mg/kg; Cohort 2: 8 mg/kg.

Five subjects experienced mild (Grade 1) transient injection site reactions (two from Cohort 1 and three from Cohort 2). No other treatment emergent adverse events related to study drug.

These mild transient injection site reactions are common with subcutaneously administered drugs. These results support the potential utility of subcutaneous administration of OP-101.

Example 4: A Double-Blind, Placebo-Controlled Phase 2 Study to Evaluate the Safety, Tolerability, Pharmacokinetics, and Efficacy of OP-101 (dendrimer N-acetyl cysteine) in Patients with Severe COVID-19

Overview

According to the CDC, ARDS has developed in 17-29% of hospitalized COVID-19 patients and in the Wuhan cohort 41.8% of patients developed ARDS. ARDS was correlated with high fever ($\geq 39°$ C.) in most patients with COVID-19. Elevated body temperatures are likely the result of a classic "cytokine storm" caused by the uncontrolled release of potent cytokines from M1 activated macrophage recruited to the lungs after infection. In patients that recover from ARDS, the M1 macrophages switch to M2 anti-inflammatory macrophages. However, the only current therapy to treat the current uncontrolled inflammation is systemic corticosteroids, an unsafe option in immune compromised patients.

Hydroxyl dendrimers conjugated with an anti-oxidant/anti-inflammatory agent provide a platform technology in selective delivery of drugs. Hydroxyl dendrimers conjugated with N-acetyl cysteine (D-NAC) showed robust ability to convert reactive M1-like macrophages into less reactive M2-like macrophages in multiple inflammatory models associated with brain, retinal and ocular injuries in over 30 animal models, six animal species (including dogs and monkeys), and human cells ex vivo. The D-NAC therapy attenuated the pro-inflammatory response of the reactive macrophages, bringing them to a 'normal' or anti-inflammatory state, enabling a therapeutic response that went well beyond inflammation, oxidative stress to neuronal, behavioral, cognitive, and other functional outcomes. Systemic therapy with D-NAC was effective in preclinical models of cerebral palsy, hypoxic-ischemia, cardiac arrest, age-related macular degeneration, retinopathy of prematurity, and diabetic retinopathy in rodents and dogs. These preclinical data indicate D-NAC is a targeted anti-inflammatory/anti-oxidant therapy which may be clinically beneficial for ARDS.

D-NAC is a highly potent anti-inflammatory/anti-oxidant compound due to the fact that it selectively delivers drug to the target macrophages and reduces side effects of free drug. The beneficial effects of D-NAC include a reduction in pro-inflammatory cytokines and reactive oxygen species. Additionally, D-NAC has been shown to be well tolerated with no clinical adverse effects in healthy adults at single doses up to 40 mg/kg IV. D-NAC is currently being studied in healthy adults at 4 and 8 mg/kg subcutaneous doses to enable more convenient repeat administration.

This study evaluated the ability of D-NAC to reduce hospitalization time, ventilator requirements, and/or death in patients with ARDS and COVID-19 caused by SARS-CoV-2. The D-NAC is being tested in K18-hACE2 transgenic mouse infected with a human SARS-CoV strain via intranasal inoculation (McCray et al J Virol 81(2):813-21 2007) and/or an LPS induced ARDS in normal mice to evaluate the ability of D-NAC to reduce pro-inflammatory macrophage and corresponding cytokine release. Work with SARS-CoV-2 was conducted in collaboration with a National or Regional Biocontainment Laboratory. In parallel, repeat dose GLP toxicology was initiated to support a clinical trial. The clinical trial enrolled COVID-19 ARDS patients undergoing a cytokine storm as assessed by presence of systemic inflammatory response syndrome, sepsis or septic shock. The clinical protocol is outlined below.

Primary Objective

The primary objective of this study is to evaluate the safety and tolerability of OP-101 after a single dose in patients with severe COVID-19.

Secondary Objective(s)

The secondary objective of this study is to determine the effect of OP-101 reducing proinflammatory cytokines after a single dose in patients with severe COVID-19.

Methods

The Phase 2 clinical trial study was a randomized, double-blind, placebo-controlled single ascending-dose design for safety and tolerability. Patients received standard of care (SOC) treatment.

The study was conducted at approximately 6 sites.

Patients were screened and enrolled within 72 hours because of the rapid progression of their disease. Once enrolled, each patient was randomized to receive either a single IV infusion of OP 101 at the currently enrolling dose level, or placebo control in a ratio of 3:1 per group (1:1:1:1 ratio overall). The patient was monitored for safety, and (Pharmacokinetic) PK and pharmacodynamic (PD) samples were obtained post-dose. Patients, or an authorized representative, provided informed consent before any study procedures are performed, and the patient must meet all of the inclusion and none of the exclusion criteria to participate in the study. Eligible patients were dosed on Day 1, and study follow-up will complete on Day 60.

Figure 2:
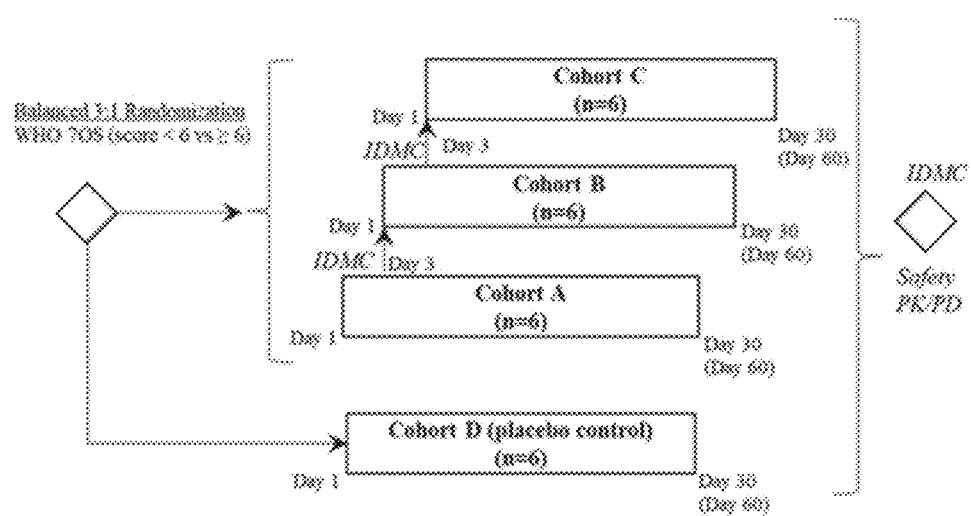
FIG. 2 is a schematic diagram showing four separate and sequential Cohorts A (2 mg/kg OP-101), B (4 mg/kg OP-101), C (8 mg/kg OP-101) and D (placebo control), with six patients in each cohort. Dose escalation from Cohort A (2 mg/kg) to Cohort B (4 mg/kg) was determined by the Independent Data Monitoring Committee (IDMC), after review of safety and tolerability through Day 3 of Cohort A.

There were 4 separate and sequential cohorts (2 mg/kg, 4 mg/kg, 8 mg/kg OP-101, and matching Placebo) with 6 patients in each cohort (FIG. 2 and Table 1). Cohort A was randomized to enroll 6 patients administered a single dose of 2 mg/kg OP-101 or 2 patients enrolled to Placebo from Cohort D. Dose escalation from Cohort A (2 mg/kg) to Cohort B (4 mg/kg) was determined by the Independent Data Monitoring Committee (IDMC), after review of safety and tolerability through Day 3 of Cohort A. Cohort B was randomized to enroll 6 patients administered a single dose of 4 mg/kg or 2 patients enrolled to Placebo from Cohort D. The same procedures were used to escalate to Cohort C (8 mg/kg). The total randomization ratio for was 1:1:1:1, with 6 patients per cohort. Stratification was based on baseline World Health Organization Blueprint COVID-19 Master Protocol Synopsis 7-Point Ordinal Scale (WHO 7OS) (score <6 vs ≥6).

TABLE 1

Study Drug Dosing

| Cohort | Dose (mg/kg) | Dose Frequency | Number of Patients |
| --- | --- | --- | --- |
| A | 2 | Single dose | 6 |
| B | 4 | Single dose | 6 |
| C | 8 | Single dose | 6 |
| D | 0 (Placebo) | Single dose | 6 |

After the single dose, plasma samples were collected for Pharmacokinetics/Pharmacodynamics (PK/PD) analysis. PK/PD Plasma samples were with sparse sampling collected as follows: pre-dose, and at 2, 12, and 24 hours post start of infusion, if possible. Additional blood samples for PD analysis were taken on Days 3, 5, and 8 and with safety laboratory tests on Days 15, 22, and 30 (±1 day). Blood/samples for PK/PD analysis can be obtained within ±30 minutes of the scheduled sampling time for sample times ≤24 hours, and within ±24 hours of the scheduled sampling times for sample times >24 hours.

Urine PK samples were collected as follows: spot sample pre-dose and during the following interval: 0-4 hrs post start of infusion (SOI), 4-8 hrs post SOI, 8-12 hrs post SOI, 12-18 hrs post SOI and 18-24 hrs post SOI.

Patients in all cohorts received best available SOC treatment by the primary clinical team, including mechanical ventilation as indicated by clinical judgment and patient response. All surviving patients were followed up for 30 days, including remote follow-up if patient was discharged from hospital.

Safety assessments included AE monitoring; clinical laboratory tests (hematology, chemistry, and urinalysis); physical examinations; and vital signs (heart rate, respiratory rate, body temperature, and systolic and diastolic blood pressure [BP]). Coagulation testing was performed at screening.

Subject Selection: Inclusion Criteria

Individuals must meet all of the following criteria to be included in the study: Male or nonpregnant female adults aged ≥18 years at time of signing the informed consent form (ICF); Positive laboratory test for SARS-CoV-2 or respiratory infection with recent exposure to a person with laboratory-proven SARS-CoV-2; Patient has an ordinal scale score between 4 and 7, inclusive, using the WHO 7O; Hypoxemia defined by $SpO_2$ of <95% on room air or ARDS; Occurrence of at least one of the following criteria: fever >38.0° C., tachycardia >90 beats/minute, tachypnea >20 breaths/minute, leucocytosis >12×10$^9$/L or leucopoenia <4×10$^9$/L. The timing of these assessments, does not need to occur on the day of screening, but can occur anytime from the date of hospital admission to the day of screening evaluation; Screening and randomization must occur within 72 hours from the initiation of mechanical ventilation (WHO score 6); A signed ICF from the patient or the patient's legally authorized representative must be available (telephone consent is acceptable); Female patients may not be pregnant, lactating, or breastfeeding; Female patients of childbearing potential must have negative result for pregnancy test at screening; Male patients must agree to using a barrier method of contraception during the study and for 90 days after the last dose; Patients must have an estimated glomerular filtration rate of >45 mL/min/1.73 m$^2$ at screening; and Must agree not to enroll in another study of an investigational agent prior to completion of this study

Subject Selection: Exclusion Criteria

Individuals meeting any of the following criteria at screening are ineligible to participate in this study: Not expected to survive for more than 24 hours; Underlying clinical condition where, in the opinion of the investigator, it would be extremely unlikely that the patient would come off ventilation (e.g., motor neuron disease, Duchenne muscular dystrophy, or rapidly progressive interstitial pulmonary fibrosis); Severe chronic obstructive pulmonary disease requiring long-term home oxygen therapy or mechanical ventilation (noninvasive ventilation or via tracheotomy) except for continuous positive airway pressure or bi-level positive airway pressure used solely for sleep-disordered breathing; Congestive heart failure, defined as New York Heart Association Class IV; Acute left ventricular failure or myocardial infarction; Currently receiving extracorporeal membrane oxygenation (ECMO) therapy; Receiving renal dialysis therapy for chronic renal failure; Moderate to severe liver failure (Childs-Pugh Score >12); Presence of any active malignancy (other than nonmelanoma skin cancer) that required treatment within the last 2 years Lung transplant patient; WHO Class III or IV pulmonary hypertension; Documented deep venous thrombosis or pulmonary embolism within past 3 months; Major trauma in the preceding 5 days; Concurrent treatment with immune modulatory study drugs (e.g., anti-IL6 antibodies, JAK kinase inhibitors) or other agents with actual or possible direct acting antiviral activity against SARS-CoV-2 within 30 days or 5 half-lives, whichever is longer, prior to dosing with OP-101; except for those that have received FDA emergency-use authorization and have become SOC. Concurrent treatment with corticosteroids is permitted if subject has documented continued hypoxemia ($SpO_2$ of <95% on room air) and hyperinflammation (elevated CRP, >upper limit of normal local lab) at screening; Has lost or donated >450 mL of whole blood or blood products within 30 days before screening.

Determination of Sample Size

The study is proof-of-concept, designed to assess the maximum tolerated dose of OP-101 based on safety and tolerability. Six patients per cohort allows for a suitable assessment of safety and tolerability. Placebo was included in order to be able to correctly interpret the results and to aid in distinguishing between adverse effects attributable to study treatment.

Treatment Assignment

Patients who met all applicable eligibility criteria on Day 1 were centrally randomized in a 3:1 ratio to either OP-101 2 mg/kg (Cohort A) or placebo (Cohort D), followed by a 3:1 ratio to either 4 mg/kg OP-101 (Cohort B) or placebo (Cohort D), and finally 3:1 ratio to either 8 mg/kg OP-101 (Cohort C) or placebo (Cohort D) using an automated IXRS. Randomization of patients will be stratified based on baseline WHO 7OS score (<6 vs ≥6) as assessed on Day 1.

Blinding

The investigators, site staff assessing the safety and efficacy, other related study staff (including Sponsor and any designees), all patients, and laboratories will remain blinded to the study treatment assignment throughout this study. Laboratory staff performing evaluation of PK assessments will be regarded as unblinded.

Administration of Study Medication

OP-101 is supplied as a lyophilized powder for reconstitution with sterile water for injection. Each vial includes 500 mg OP-101. After reconstitution, the OP-101 solution was added to a 100 mL IV saline bag at the appropriate dose based upon the dose cohort and patient's body weight (kg). Placebo was supplied as a 100-mL IV saline bag by an unblinded pharmacist. All doses in Cohorts A-D were administered as a continuous IV infusion (100 mL) over 60 minutes.

Study Stopping Rules

This study will stop and no further dosing and/or dose escalation will occur until safety information can be reviewed in the event that one patient within a dose cohort has a drug-related SAE, or ≥2 patients within the same dose cohort have a drug-related Grade 3 AE or SAE.

Study Procedures and Schedule of Assessment

Assessments and their timing are to be performed as outlined in Table 2 of Schedule of Assessments below.

TABLE 2

Schedule of Assessments

| Study Procedure | Screening Period Days <-2 | Treatment Period[a] Day 1 | Day 2 | Day 3 | Day 5 | Day 8 | Day 15 | Day 22 | Day 30 Early Termination[b] | Safety Follow Up (phone visit) Day 60 |
|---|---|---|---|---|---|---|---|---|---|---|
| Informed consent | X | | | | | | | | | |
| Inclusion/exclusion criteria | X | | | | | | | | | |
| 7-point ordinal scale score[c] | X | X | X | X | | X | X | X | X | |
| NEWS2 score | X | X | X | X | | X | X | X | X | |
| Medical history | X | | | | | | | | | |
| Demographics | X | | | | | | | | | |
| Prior/concomitant medications | X | X | X | X | | X | X | X | X | |
| Physical examination (complete) | X | | | | | | | | X | |
| Height | X | | | | | | | | | |
| Vital signs[d] | X | X | X | X | | X | X | X | X | |
| Oxygen level/fraction of inspired oxygen ($SpO_2/FiO_2$)[e] | X | X | X | X | | X | X | X | X | |
| Pregnancy test[f] | X | | | | | | | | | |
| Safety laboratory tests (chemistry, hematology, and urinalysis)[g] | X | X | X | X | | X | X | X | X | |
| Urine KIM-1 and NGAL (Central Lab)[g] | | X | X | X | | X | X | X | X | |
| aPTT, PTT, INR | X | | | | | | | | | |
| Plasma PK sampling[h] | | X | X | | | | | | | |
| Urine PK sampling[i] | | X | X | | | | | | | |

TABLE 2-continued

Schedule of Assessments

| Study Procedure | Screening Period Days <−2 | Treatment Period[a] Day 1 | Day 2 | Day 3 | Day 5 | Day 8 | Day 15 | Day 22 | Day 30 Early Termination[b] | Safety Follow Up (phone visit) Day 60 |
|---|---|---|---|---|---|---|---|---|---|---|
| PD sampling for CRP and ferritin (Local labs)[j] | | X | X | X | X | X | X | X | X | |
| PD sampling for IL-6 (Central lab) [k] | | X | X | X | X | X | X | X | X | |
| Administer study drug[l] | | X | | | | | | | | |
| Assess adverse events[m] | X | X | X | X | | X | X | X | X | X |
| Mortality status | | | | | | | | | X | X |

Abbreviations: aPTT, activated partial thromboplastin time; FiO2, fraction of inspired oxygen; INR, international normalized ratio; PD, pharmacodynamic; PK, pharmacokinetic; PTT, partial thromboplastin time; SpO2, oxygen saturation.
Note:
A 30-minute window for vital signs and all post dose procedures is allowed. All visits post hospital discharge have ±2 days visit window. Study Day 60 has ±7 days visit window. When multiple procedures are scheduled at the same time point, the order of procedures should be as follows: obtain vital signs, check oxygen level, and collect blood sample (drawn at nominal time).
[a]Single IV dose on Day 1, 30 days safety/PD follow-up, and 60 days safety/mortality follow-up. Some study procedures will take place daily as noted in the footnotes.
[b]Assessments will be performed prior to discharge.
[c]WHO 7OS measured at screening and daily thereafter until discharge from hospital. Also see Inclusion Criterion 4. WHO 7OS is not collected, after hospital discharge.
[d]Vital signs (heart rate, respiratory rate, body temperature, and systolic and diastolic blood pressure) will be recorded at all study visits after the patient has been seated or supine for ±5 minutes. Vital signs will be measured at a minimum daily until discharge from hospital. Body weight (without shoes) will be recorded whenever vital signs are recorded; height (without shoes) will be recorded at screening only. After discharge from hospital collected at Day 15, 22, and 30 or if clinically indicated.
[e]Oxygen saturation by pulse oximetry and fraction inspired oxygen levels will be measured and reported in mm Hg or kPa and the ratio, SpO2/FiO2, will be calculated. Measurements will be made a minimum of daily until discharge from hospital. After discharge from hospital collected at Day 15, 22, and 30 or if clinically indicated.
[f]A urine or serum pregnancy test will be performed at screening for female patients of childbearing potential.
[g]Safety laboratory tests will be performed. Day 1 sample will be taken within 30 minutes prior to dosing. See Section 14.4 for the list of analytes assessed; estimated glomerular filtration rate will be assessed and will be based on the patient's creatinine level, age, sex, and race. Safety laboratory tests will be taken at screening (excluding KIM-1 and NGAL) and on Days 1, 2, and 3 and then weekly on Days 8, 15, 22, and 30. Creatinine will be measured daily, if possible, until discharge from hospital. After discharge from hospital creatinine collected at Day 15, 22, and 30 or if clinically indicated.
[h]Plasma PK plasma samples will be with sparse sampling collected as follows: predose and at 2, 12, and 24 hours, if possible. Blood samples for PK analysis can be obtained within ±30 minutes of the scheduled sampling time for sample times ≤24 hours, and within ±24 hours of the scheduled sampling times for sample times >24 hours.
[i]Urine PK samples will be collected as follows: pre-dose and at 2, 12, and 24 hours post start of infusion, if possible. Urine PK samples have the same collection window as plasma PK samples.
[j]Additional blood samples for PD analysis at local lab (CRP, ferritin) will be taken at 2, 12, and 24 hours (Day 2) and Day 5, if possible, and at the same time as safety laboratory tests on Days 3, 8, 15, 22, and 30 (±1 day).
[k] Additional blood samples for PD analysis at central lab (IL-6) will be taken at 2, 12, and 24 hours (Day 2) and Day 5, if possible, and at the same time as safety laboratory tests on Days 3, 8, 15, 22, and 30.
[l]Cohort dosing will be separate and sequential with a single dose on Day 1.
[m]Adverse events will be recorded as presented throughout the study.

Assessments and procedures scheduled at a visit where study drug is administered should be performed before administration of treatment unless otherwise indicated in the Schedule of Assessments.

Efficacy assessments include time to improvement in clinical status, number of days in ICU, number of days of hospitalization for survivors, time to discharge from clinic or hospital or to a NEWS2 of ≤2 and maintained for 24 hours, change from baseline (predose, Day 1) in NEWS2 scoring system. Safety assessments include vital signs, physical examinations, laboratory assessments, and Adverse events (AEs). PK assessments including percentage change in proinflammatory markers (CRP, ferritin, and IL-6) after administration of OP-101.

Primary Endpoint

Safety and tolerability of a single IV dose of OP-101.

Secondary Endpoints

1. Time to improvement (2 points) in clinical status assessment using the WHO 7OS
2. Time to resolution of fever for at least 48 hours without antipyretics for patients with documented fever (≥37.2° C. [oral], or ≥37.8° C. [rectal], or ≥38.0° C. [tympanic])
3. Time to improvement in oxygenation for at least 48 hours defined by increase in pulse oxygen saturation (SpO$_2$)/FiO$_2$ of ≥50 compared with nadir SpO$_2$/FiO$_2$
4. Mean change in WHO 7OS
5. Time to discharge from clinic or hospital or to NEWS2 of ≤2 and maintained for 24 hours
6. Proportion of patients alive and not using supplemental oxygen at time of discharge from hospital/clinic or Day 30
7. Number of days of resting respiratory rate of >24 breath/min
8. Number of days with hypoxemia
9. Number of days of supplemental oxygen use
10. Number of ventilator-free days in the first 28 days
11. Number of days in intensive care unit (ICU)
12. Number of days of hospitalization for survivors
13. Number of all cause deaths
14. Percentage change in proinflammatory cytokines (CRP, ferritin, and IL-6)
15. Incidence of drug-related serious adverse events (SAEs)

Exploratory Endpoints

Change in National Early Warning Score 2 (NEWS2) from Day 1 to Day 30.

Pharmacokinetic Endpoints

Pharmacokinetic (PK) endpoints will be estimated by Population PK modeling.

Pharmacodynamic Endpoints

Inflammatory cytokines to be measured in the study include CRP, ferritin, and IL-6.

Analysis Sets

Enrolled Set

The Enrolled Set will include all subjects who sign the ICF or those who had their legally authorized representative sign for them.

Safety Set

The Safety Set (SAF) includes all subjects who were administered at least one dose of study medication. Subjects will be analyzed according to treatment actually received. The SAF will be used for all analyses of safety endpoints and for the presentation of subjects in all subject listings and for summaries of subject disposition. The SAF will be used for all analyses of safety endpoints.

Intent-to-Treat Set

The Intent-to-Treat (ITT) Set includes all randomized subjects. Subjects will be analyzed according to randomized treatment. The treatment group assignment will be designated according to initial randomization. The ITT Set will be used for all analyses of efficacy endpoints.

Pharmacokinetic Set

The Pharmacokinetic Set (PKS) includes all subjects in the SAF and have at least one postbaseline PK concentration measured. The treatment group assignment in the population will be defined by the treatment actually received. PK concentrations are listed for all subjects in PK set.

Pharmacodynamic Set

The pharmacodynamic set (PDS) will include all subjects in the SAF, with at least 1 measurable postbaseline PD assessment. The treatment group assignment in this population will be defined by the treatment actually received. This population will be used for the analyses of PD.

Protocol Deviations

Protocol Deviations will be documented from project start to project close. The process of identifying and tracking protocol deviations are described in the Protocol Deviation and Non-compliance Management Plan that is prepared by project lead.

Protocol deviations and/or violations and the reasons they occurred will be included in the clinical study report.

Efficacy

The ITT analysis set will be used for the efficacy endpoint analyses.

Estimands

This Phase 2 study is proof-of-concept, with the primary objective of assessing safety and tolerability in a range of ascending doses of OP-101. The primary population for this assessment will be the SAF, and any initial assessment of efficacy will be conducted in the ITT analysis set. The analyses of the endpoints achieve the primary focus of the study and are not so focused as to omit any possible unforeseen safety issues. Decision regarding choices of OP-101 dose to be tested in future studies will be determined by review of safety, and changes in CRP. Any initial efficacy seen at this point may also be accounted for in decision-making.

Intercurrent events will be handled as per the treatment policy strategy, i.e., per International Council for Harmonisation (ICH) E9 Addendum: "The occurrence of the intercurrent event is considered irrelevant in defining the treatment effect of interest: the value for the variable of interest is used regardless of whether or not the intercurrent event occurs."

All secondary endpoints are chosen to provide a suitable assessment of clinical function in this indication. Details regarding handling of data for time-to-event endpoints due to dropout or death are included.

Any missing data for binary endpoints will be imputed as nonresponder; for continuous endpoints, or those based on ordinal scales (such as the primary endpoint), multiple imputation will be used, per Section 6.3.

Efficacy Endpoint(s) and Analyses

Assessments using WHO 7OS: The WHO 7OS are used to assess time to improvement (2 points) in clinical status and the mean change in WHO 7OS: WHO 7-point ordinal scale ranges from 0 (uninfected) to 7 (hospitalized)
1. No clinical or virological evidence of infection (uninfected)
2. No limitation of activities (ambulatory)
3. Limitation of activities (ambulatory)
4. Hospitalized, no oxygen therapy (hospitalized mild disease)
5. Hospitalized, oxygen by mask or nasal prongs (hospitalized mild disease)
6. Hospitalized, noninvasive ventilation or high-flow oxygen (hospitalized severe disease)
7. Hospitalized, intubation and mechanical ventilation (hospitalized severe disease)
8. Hospitalized, ventilation+additional organ support–pressors, renal replacement therapy, ECMO

Results

No subjects had treatment emergent adverse events related to drug or placebo administration. Some of the unblinded survival data in Phase 2 COVID-19 Trial is summarized in Table 3. Each Cohort had six patients treated with OP-101 and two placebo patients. One placebo treated patient in Cohort B with 4 mg/kg patients died and both placebo patients in Cohort C with the 8 mg/kg patients died. The numbers are small but the data to date suggest a trend toward survival benefit.

TABLE 3

| Unblinded Survival Data in Phase 2 COVID-19 Trial | | |
|---|---|---|
| Dose Group | Death | % Survival |
| 2 mg/kg | 2 | 66.7 |
| 4 mg/kg | 0 | 100 |
| 8 mg/kg | 1 | 83.3 |
| Placebo | 4 | 33.3 |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for treating one or more symptoms of severe inflammation in an organ of a subject in need thereof, the method comprising:
administering to the subject a composition comprising dendrimers complexed, covalently conjugated, or intra-molecularly dispersed or encapsulated with N-acetyl cysteine, in an amount effective to treat one or more symptoms of severe inflammation,
wherein the severe inflammation is hyperinflammation associated with elevated levels of C-reactive protein (CRP),
wherein the composition is administered in an amount effective to reduce inflammation in the lung.

2. The method of claim 1, wherein the severe inflammation is systemic inflammation involving multiple organs, tissues, and/or cell types of the body.

3. The method of claim 1, wherein the severe inflammation is associated with sepsis or septic shock.

4. The method of claim 1, wherein the severe inflammation is caused by macrophage activation syndrome.

5. The method of claim 1, wherein the severe inflammation is associated with multi-organ dysfunction including neuroinflammation.

6. The method of claim 1, wherein the severe inflammation is associated with over-reactive M1 macrophages and/or elevations in proinflammatory markers selected from the group consisting of IL-6, ferritin, and IL-1b.

7. The method of claim 1, wherein the severe inflammation is characterized by cytokine storm.

8. The method of claim 1, wherein the severe inflammation is associated with acute lung injury (ALI) and/or acute respiratory distress syndrome (ARDS) associated with or arising from ventilator use, viral infection, sepsis, or systemic bacterial infections.

9. The method of claim 8, wherein the dendrimers are covalently conjugated, or intra-molecularly dispersed or encapsulated with N-acetyl cysteine in an amount effective to treat, alleviate or prevent one or more symptoms of acute lung injury or acute respiratory distress syndrome.

10. The method of claim 8, wherein the acute lung injury is ventilator-induced lung injury.

11. The method of claim 8, wherein the acute respiratory distress syndrome is caused by infection with a virus.

12. The method of claim 11, wherein the virus is SARS-COVID-2.

13. The method of claim 1, wherein the dendrimers are hydroxyl-terminated dendrimers.

14. The method of claim 1, wherein the dendrimers are generation 4, generation 5, or generation 6 poly(amidoamine) dendrimers.

15. The method of claim 1, wherein the composition is formulated for intravenous, subcutaneous, or intramuscular administration.

16. The method of claim 1, wherein the composition is formulated for delivery enterally or to a mucosal surface.

17. The method of claim 1, wherein the composition is administered via intravenous, subcutaneous, or intramuscular route.

18. The method of claim 1, wherein the composition is administered prior to, in conjunction, subsequent to, or in alternation with treatment with one or more additional therapies or procedures.

19. The method of claim 18, wherein the one or more additional therapies are selected from the group consisting of antimicrobials, surfactant, and corticosteroids.

20. The method of claim 18, wherein the one or more additional procedures are selected from the group consisting of prone positioning, recruitment maneuver, inhalation of NO, extracorporeal membrane oxygenation (ECMO), intubation, and inhalation of $PGI_2$.

21. The method of claim 1, wherein the composition is in an amount between about 0.1 mg/kg body weight of the subject, and about 40 mg/kg body weight of the subject.

22. The method of claim 1, wherein the composition is in an amount between about 2 mg/kg body weight of the subject, and about 8 mg/kg body weight of the subject, and
wherein the composition is administered by subcutaneous injection.

23. The method of claim 1, wherein the dendrimer conjugated to N-acetyl cysteine is in an amount between about 20 mg/kg body weight of the subject, and about 40 mg/kg body weight of the subject, and
wherein the composition is administered by intravenous infusion.

24. The method of claim 1, wherein the composition comprises one or more of histidine pH 5.5, and trehalose dihydrate.

25. A method for treating one or more symptoms of severe inflammation in an organ of a subject in need thereof, the method comprising:
administering to the subject a composition comprising dendrimers complexed, covalently conjugated, or intra-molecularly dispersed or encapsulated with N-acetyl cysteine, in an amount effective to treat one or more symptoms of severe inflammation,
wherein the severe inflammation is hyperinflammation associated with elevated levels of CRP,
wherein the composition is administered in an amount effective to reduce vascular leakage or vascular permeability in the lung, increase alveolar cell integrity or endothelial cell integrity in the lung, increase the ratio of arterial oxygen to the fraction of inspired oxygen ($PaO_2/FiO_2$), increase pulse oximetry-based peripheral blood oxygen saturation ($SpO_2/FiO_2$) ratios, and/or reduce bronchoalveolar lavage (BAL) protein levels or bronchoalveolar lavage cell count.

26. A method for treating one or more symptoms of severe inflammation in an organ of a subject in need thereof, the method comprising:
administering to the subject a composition comprising dendrimers complexed, covalently conjugated, or intra-molecularly dispersed or encapsulated with N-acetyl cysteine, in an amount effective to treat one or more symptoms of severe inflammation,
wherein the severe inflammation is hyperinflammation associated with elevated levels of CRP,
wherein the composition is administered in an amount effective to reduce one or more pro-inflammatory cells, chemokines, and/or cytokines in the lung.

27. The method of claim 26, wherein the composition is administered in an amount effective to reduce one or more pro-inflammatory chemokines selected from the group consisting of MCP-1, CXCL-8, CXCL-1, CXCL-5, and CCL-2.

28. The method of claim 26, wherein the composition is administered in an amount effective to reduce one or more pro-inflammatory cytokines selected from the group consisting of C-reactive protein (CRP), ferritin, IL-6, TNF-α, IL-12, IL-1β, and IL-18.

29. The method of claim 26, wherein the one or more pro-inflammatory cells are M1-like macrophages.

* * * * *